United States Patent
Hishikawa et al.

(10) Patent No.: US 10,278,668 B2
(45) Date of Patent: May 7, 2019

(54) MOBILE X-RAY APPARATUS AND METHOD FOR CHARGING MOBILE X-RAY APPARATUS

(71) Applicant: HITACHI, LTD., Chiyoda-ku, Tokyo (JP)

(72) Inventors: Shingo Hishikawa, Tokyo (JP); Kaoru Yamamoto, Tokyo (JP); Masakazu Okabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 284 days.

(21) Appl. No.: 15/302,338

(22) PCT Filed: Apr. 3, 2015

(86) PCT No.: PCT/JP2015/060598
§ 371 (c)(1),
(2) Date: Oct. 6, 2016

(87) PCT Pub. No.: WO2015/156224
PCT Pub. Date: Oct. 15, 2015

(65) Prior Publication Data
US 2017/0020480 A1    Jan. 26, 2017

(30) Foreign Application Priority Data

Apr. 7, 2014    (JP) .................................. 2014-078695

(51) Int. Cl.
*A61B 6/00*    (2006.01)

(52) U.S. Cl.
CPC .............. *A61B 6/56* (2013.01); *A61B 6/4405* (2013.01); *A61B 6/461* (2013.01); *A61B 6/467* (2013.01); *A61B 6/54* (2013.01)

(58) Field of Classification Search
None
See application file for complete search history.

(56) References Cited

U.S. PATENT DOCUMENTS

| 2008/0240358 A1* | 10/2008 | Utschig | ................... A61B 6/56 378/107 |
| 2015/0054466 A1* | 2/2015 | Kinomura | ........... B60L 11/1816 320/134 |
| 2017/0279273 A1* | 9/2017 | Tischer | ..................... H02J 3/14 |

FOREIGN PATENT DOCUMENTS

| JP | 10510135 A | 9/1998 |
| JP | 2006158508 A | 6/2006 |

(Continued)

OTHER PUBLICATIONS

International Search Report dated Jun. 23, 2015 for International Patent Application No. PCT/JP2015/060598.

*Primary Examiner* — Hoon K Song

(57) ABSTRACT

Provided is a mobile X-ray apparatus that is capable of safely charging multiple mobile X-ray apparatuses. A power supply device 10 includes a plug 7; an electrical outlet 8; a battery 12; a control unit 20; a current detector 26; and a power supply circuit 30. The power supply circuit 30 includes a power limiting circuit 40; an external output circuit 50; and a charging circuit 60. The power limiting circuit 40 limits power together with the control unit 20. In the power supply circuit 30, i) if an external output circuit 50 side is current-limited, charging is preferentially performed, and ii) if the charging circuit 60 side is current-limited, power is output preferentially to external equipment. In the power supply circuit 30, the current of one current path is limited, and a large amount of current is allowed to flow preferentially in the other current path.

8 Claims, 25 Drawing Sheets

(56) References Cited

FOREIGN PATENT DOCUMENTS

| JP | 2011172906 A | 9/2011 |
|----|--------------|--------|
| JP | 2012029844 A | 2/2012 |
| JP | 2013027654 A | 2/2013 |
| JP | 2013221211   | 10/2013 |

* cited by examiner

FIG.21
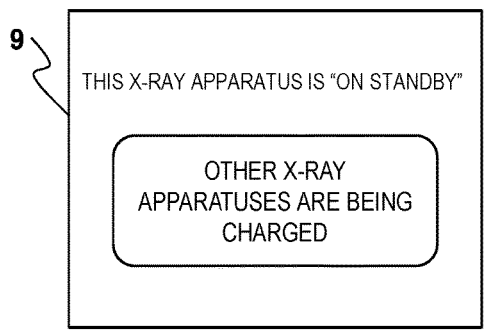
(a)
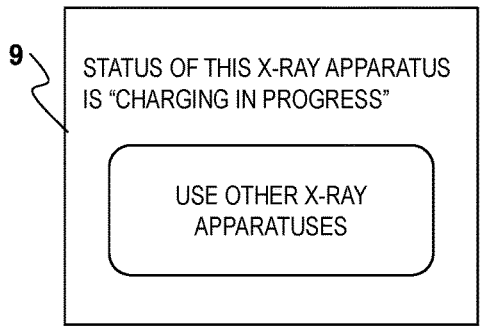
(b)
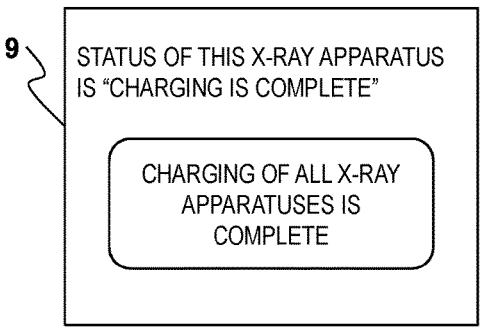
(c)
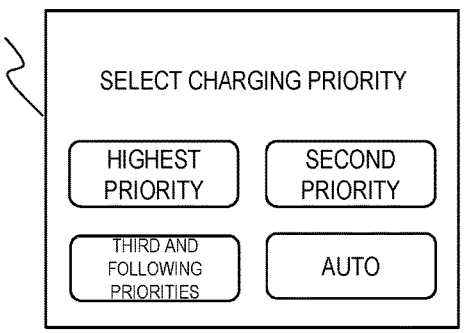
(d)
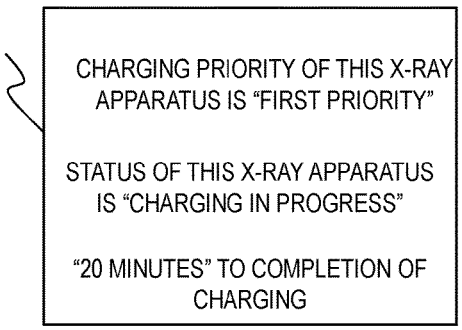
(e)

MOBILE X-RAY APPARATUS AND METHOD FOR CHARGING MOBILE X-RAY APPARATUS

CROSS-REFERENCE TO RELATED APPLICATIONS

This application is a national phase claiming the benefit of and priority to International Patent Application No. PCT/JP2015/060598, entitled "MOBILE X-RAY APPARATUS AND METHOD FOR CHARGING MOBILE X-RAY APPARATUS", filed Apr. 3, 2015, which claims priority to Japanese Patent Application No. 2014-078695, entitled "MOBILE X-RAY APPARATUS AND METHOD FOR CHARGING MOBILE X-RAY APPARATUS", filed Apr. 7, 2014, which are hereby incorporated by reference in their entireties.

TECHNICAL FIELD

The present invention relates to a mobile X-ray apparatus and a method for charging a mobile X-ray apparatus, particularly, to a mobile X-ray apparatus, the charging of which is very convenient.

BACKGROUND ART

A mobile X-ray apparatus can be moved inside and outside a medical facility, and is capable of taking an X-ray. The mobile X-ray apparatus takes an X-ray using power stored in an internal battery. For this reason, a user is required to charge a battery in advance before using the mobile X-ray apparatus. PTL 1 discloses a mobile X-ray apparatus which switches to a chargeable state if a battery residual capacity is lower than the amount of power required to take an X-ray, and notifies a user that the battery residual capacity is low (refer to PTL 1).

CITATION LIST

Patent Literature

PTL 1: JP-A-2012-95715

SUMMARY OF INVENTION

Technical Problem

There is a problem in that in a case where there are multiple mobile X-ray apparatuses having low battery residual capacities, in the related art, it requires a substantial operational procedure for a user to charge all the mobile X-ray apparatuses. The reason for this is that in many cases, a sufficient number of electrical outlets are not provided inside a facility, and the number of electrical outlets is not enough to charge multiple mobile X-ray apparatuses. Since a large amount of current is required to charge mobile X-ray apparatuses, it is not recommended to use a power tap including an increased number of electrical outlets.

The invention is made in light of this problem, and provides a mobile X-ray apparatus that is capable of safely charging multiple mobile X-ray apparatuses.

Solution to Problem

In order to solve the problem, according to an aspect of the invention, there is provided a mobile X-ray apparatus that takes an X-ray using power charged therein, the apparatus including: a power supply device that divides a power, which is input from external equipment, into at least two powers, connects one power of the divided powers to an external output circuit, outputs the power to external equipment, connects the other power to a charging circuit, and charges the apparatus with the power. The power supply device includes a current detector that detects a current value of the input power; a power limiting circuit that limits at least one of the power output to the external output circuit and the power output to the charging circuit; and a control unit that controls current flowing in the power limiting circuit based on the current value detected by the current detector.

Advantageous Effects of Invention

According to the aspect of the invention, it is possible to provide a mobile X-ray apparatus that is capable of safely charging multiple mobile X-ray apparatuses.

BRIEF DESCRIPTION OF DRAWINGS

FIG. 21 shows diagrams illustrating examples of display on an input and output unit 9.

DESCRIPTION OF EMBODIMENTS

Hereinafter, embodiments of the invention will be described with reference to the drawings.

(1 Mobile X-ray Apparatus 1)

(1.1 Overview of Mobile X-ray Apparatus 1)

A mobile X-ray apparatus 1 of the invention will be described with reference to FIG. 1. The mobile X-ray apparatus 1 can be charged by other mobile X-ray apparatuses and is capable of charging other mobile X-ray apparatuses in addition to charging a battery with power from a wall electrical outlet of a facility.

Figure 1:
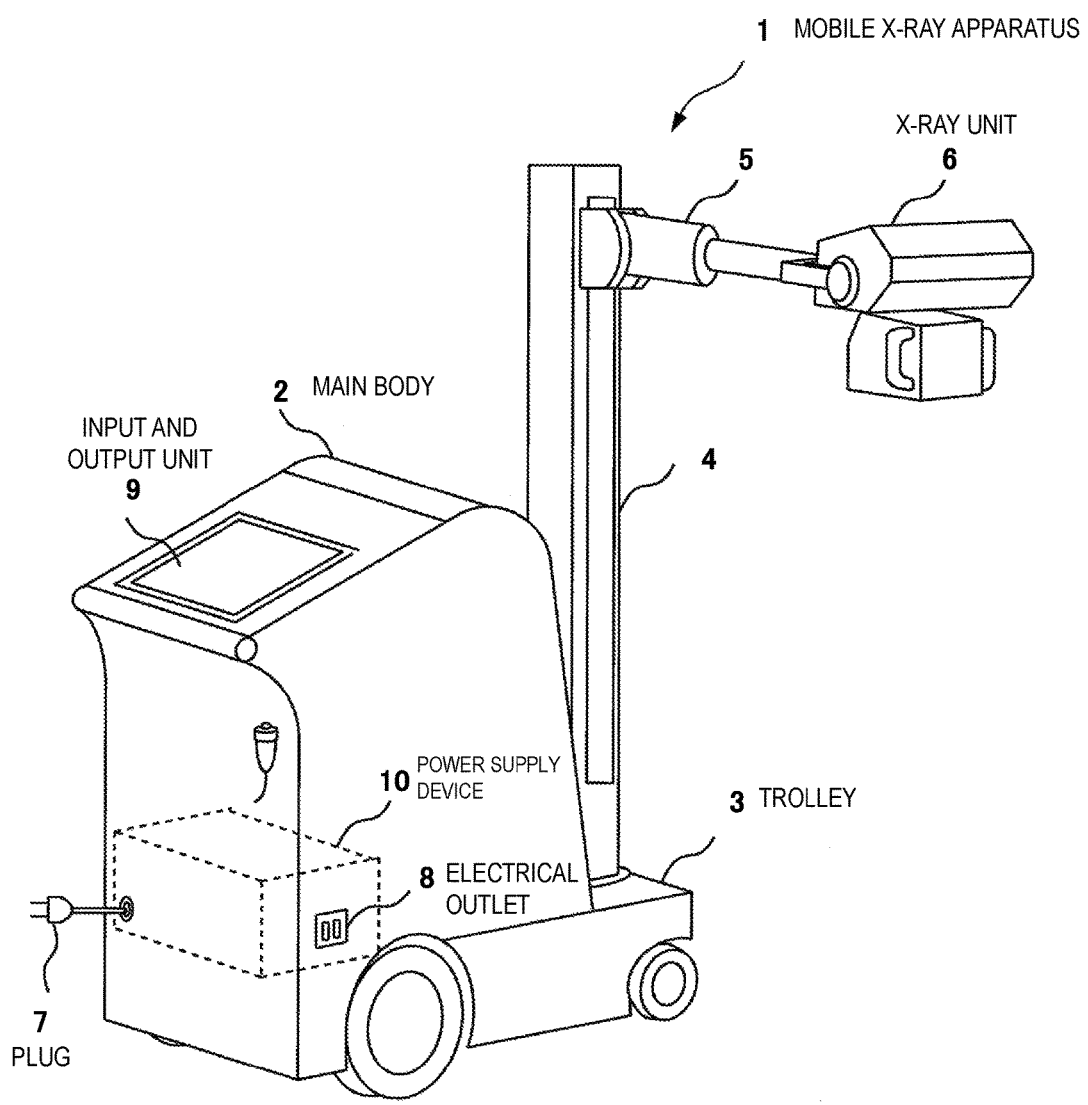
FIG. 1 is a schematic view of a mobile X-ray apparatus 1.

FIG. 1 is a schematic view of the mobile X-ray apparatus 1.

The mobile X-ray apparatus 1 includes a main body 2, and an X-ray unit 6 that generates X rays. The X-ray unit 6 is supported by a movable arm 5 and a support column 4. The X-ray unit 6 is mounted on a wheeled trolley 3 together with the main body 2.

The main body 2 includes an input and output unit 9 and a power supply device 10. The main body 2 further includes various devices required to operate the mobile X-ray apparatus 1, and description thereof will not be given herein.

The input and output unit 9 is a device through which a user confirms various information or gives an instruction to the mobile X-ray apparatus 1. For example, the input and output unit 9 is a touch panel monitor. The input and output unit 9 may be a display device such as a liquid crystal panel, a keyboard, a mouse, an input pen, a touch panel, or the like. The input and output unit 9 displays the charged status of a battery 12 (refer to FIG. 2) of the power supply device 10, or receives charging priorities from a user (in third and fourth embodiments)

(1.2 Power Supply Device 10)

The power supply device 10 will be described with reference to FIG. 2. The power supply device 10 is a device that stores power and supplies power used in taking an X-ray and the main body 2. The power supply device 10 is a power supply device that is capable of making the most of the current capacity of a power supply such as a wall electrical outlet or an external power supply.

The power supply device 10 includes a plug 7; an electrical outlet 8; a communication unit 11; the battery 12; a control unit 20; a current detector 26; a power supply circuit 30. The power supply device 10 further includes a power supply device that supplies power to a power circuit for generating X rays, a power supply circuit for an information processing device inside the main body 2, and a power supply circuit for driving the wheels of the trolley 3. The power supply device may use existing power supply technology, and description will not be given herein.

The plug 7 takes power from external equipment such as a wall electrical outlet or other mobile X-ray apparatuses. The electrical outlet 8 outputs power from the power supply device 10 to external equipment. The communication unit 11 communicates with other mobile X-ray apparatuses connected thereto (third and fourth embodiments).

The battery 12 stores power supplied from the power supply device 10. A device storing electricity is not limited to a battery, and may be a high capacitance capacitor such as an electric double layer capacitor. If an electric double layer capacitor is used, it is possible to obtain an effect of considerably decreasing the length of a power transfer time.

(1.3 Control Unit 20)

The control unit 20 controls the power limitation of the power supply circuit 30. Specifically, the control unit 20 controls power by limiting current flowing in a power limiting circuit 40 inside the power supply circuit 30. The control unit 20 includes a connection monitoring unit 21, a priority setting unit 22, a limit value acquisition unit 23, a power limit signal unit 24, and the like as functional configuration elements.

The connection monitoring unit 21 detects whether the plug 7 is connected to a wall electrical outlet or another mobile X-ray apparatus (third and fourth embodiments).

The priority setting unit 22 acquires priorities defined by a user via the input and output unit 9, and priorities defined by other mobile X-ray apparatuses, and sets charging priorities (third and fourth embodiment).

The limit value acquisition unit 23 acquires a current limit value from a storage unit (not illustrated), and sets a threshold value for switching the control of the control unit 20 from the acquired current limit value (first to fourth embodiments).

The current limit value represents the amount of current that can be acquired from external equipment by the power supply device 10. In a case where power is acquired from a wall electrical outlet, a current limit value is the current capacity (for example, 15 [A]) of the wall electrical outlet.

The current detector 26 detects current that enters the power supply circuit 30 from the plug 7. A detected current value is input to the control unit 20.

The control unit 20 may be a control device such as a microcontroller, or an internal information processing device of the main body 2.

Figure 4:
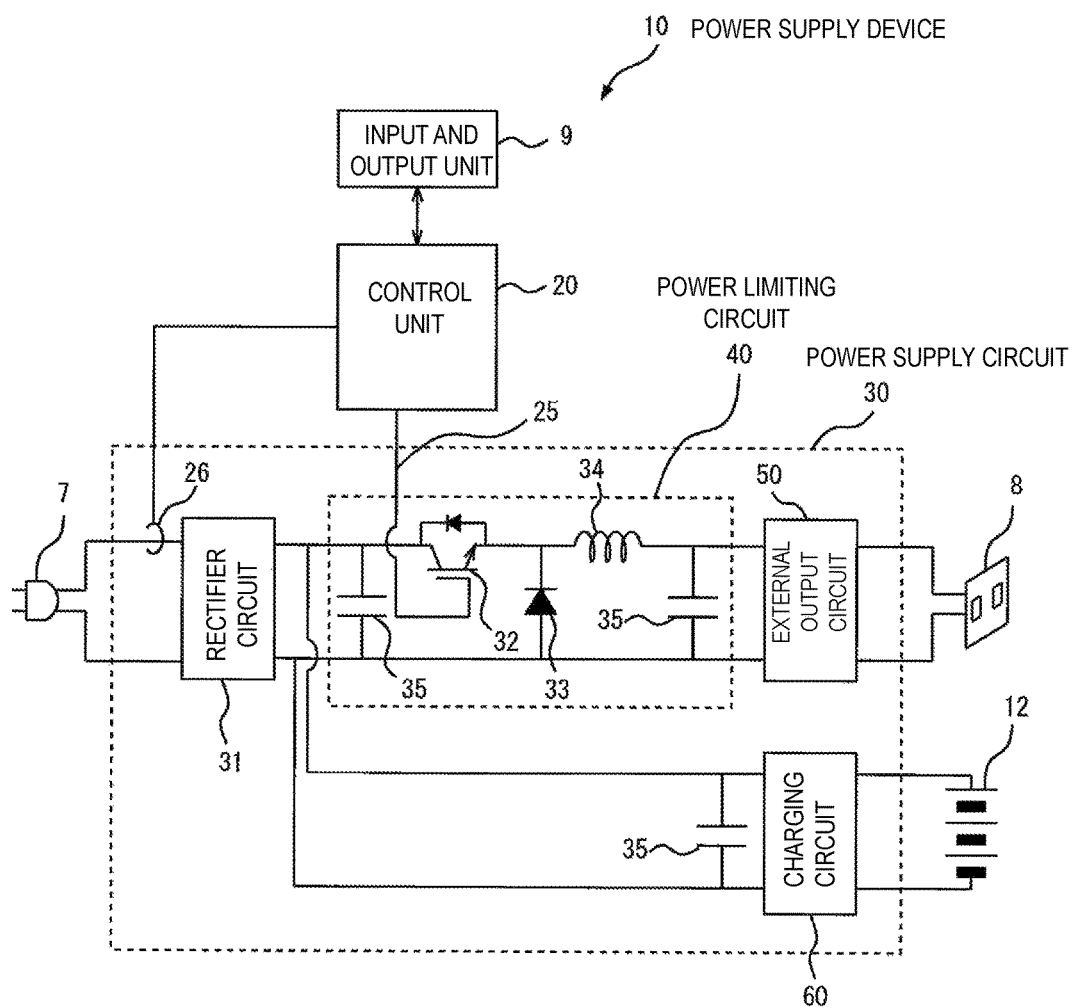
FIG. 4 is a diagram illustrating the function and circuit configuration of the power supply device 10 of a first embodiment.

The power limit signal unit 24 supplies a switch drive signal 25 to a semiconductor switch 32 (refer to FIG. 4). The switch drive signal 25 is a signal that drives the semiconductor switch 32 in an on and off manner. While monitoring an input current detected by the current detector 26, the power limit signal unit 24 adjusts on and off intervals of the switch drive signal 25 such that the input current does not exceed the current limit value.

(1.4 Power Supply Circuit 30)

The power supply circuit 30 is a circuit that outputs power, which has been supplied from the plug 7, to external equipment via the electrical outlet 8, or charges the battery 12 with power supplied from the plug 7. The power supply circuit 30 includes a rectifier circuit 31; a power limiting circuit 40; an external output circuit 50; a charging circuit 60; and the like.

(1.4.1 Rectifier Circuit 31)

The rectifier circuit 31 is a circuit that converts alternating current power into direct current power.

(1.4.2 Power Limiting Circuit 40)

The power limiting circuit 40 is a circuit which limits power together with the control unit 20. The power limiting circuit 40 is a so-called chopper circuit that is a combination of the semiconductor switch 32, a diode 33, an inductor 34, and a capacitor 35. The power limiting circuit 40 limits power supplied to a back stage by limiting the amount of current flowing in the power limiting circuit 40 (refer to FIG. 4).

The switch drive signal 25 of the semiconductor switch 32 is supplied from the control unit 20 to the power limiting circuit 40.

(1.4.3 External Output Circuit 50)

Figure 5:
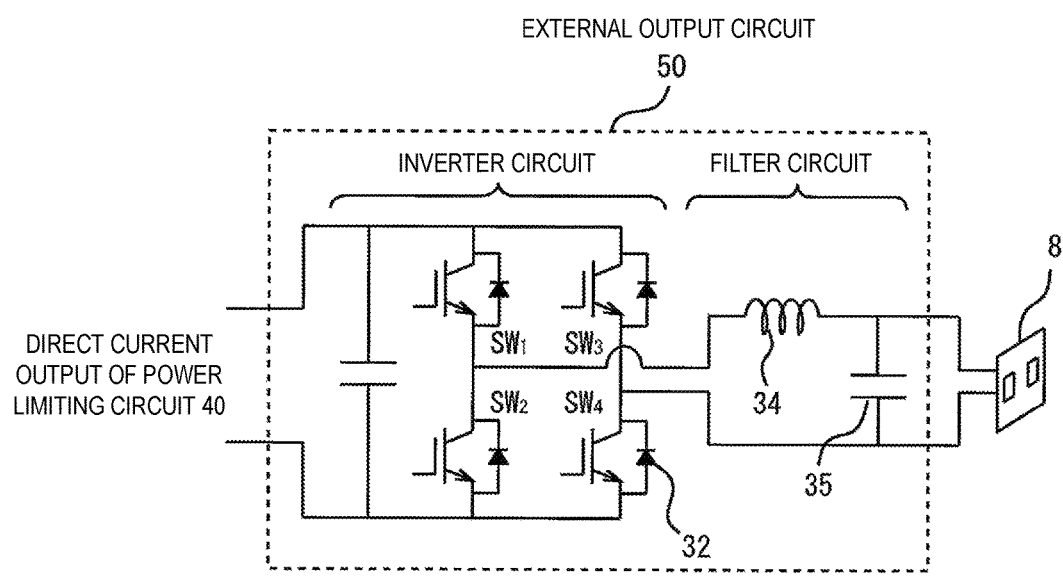
FIG. 5 is a diagram illustrating the circuit configuration of an external output circuit 50.

The external output circuit 50 is a circuit that converts direct current into alternating current. The external output circuit 50 includes an inverter circuit including a capacitor and semiconductor switches $SW_1$ to $SW_4$, and a filter circuit including an inductor 34 connected to the inverter circuit, and a capacitor 35 (refer to FIG. 5). The inverter circuit controls each of the semiconductor switches 32 ($SW_1$ to $SW_4$) in an on and off manner via an inverter control circuit (not illustrated), and outputs the same type of power as that of a commercial power supply.

(1.4.4 Charging Circuit 60)

The charging circuit 60 is a circuit that charges the battery 12. The charging circuit 60 converts an output of the rectifier circuit 31 or power supplied from the plug 7 to power of a voltage and current which is suitable for storage in the battery 12.

(1.5 Two Current Path in Power Supply Circuit 30)

Figure 2:
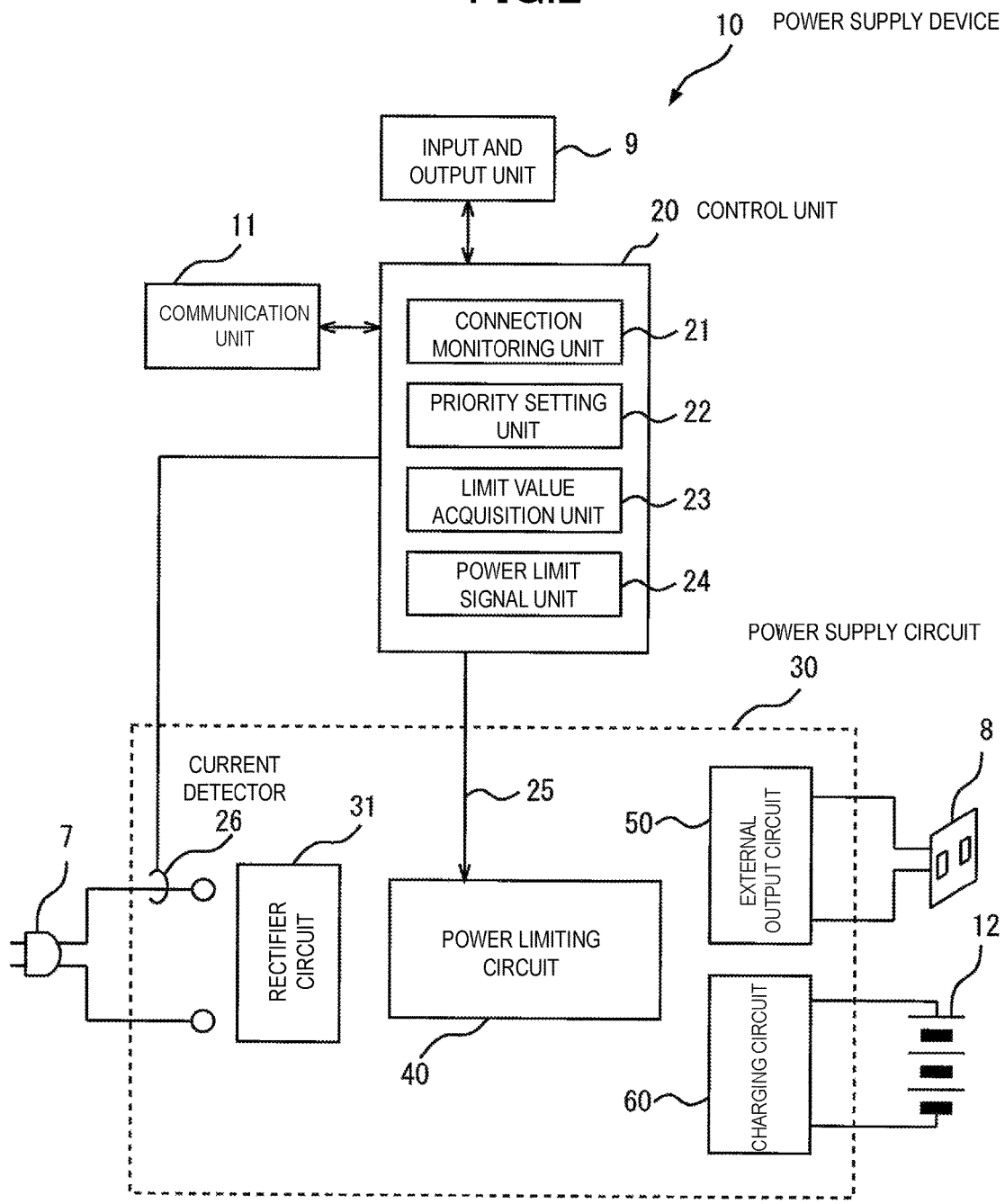
FIG. 2 is a diagram illustrating the function and circuit configuration of a power supply device 10.

FIG. 2 does not illustrate wire connections between the circuits inside the power supply circuit 30. The inventors of the invention could attain the following objectives by forming two current paths in the power supply circuit 30 by a combination of these circuits, and limiting the current of only one of the two current paths:

quick charging by making the most of current up to the current capacity of a power supply safe charging without exceeding the current capacity of the power supply in a case where power supply devices of multiple mobile X-ray apparatuses 1 are connected to each other, the multiple mobile X-ray apparatuses 1 are charged in a state where the charging of the mobile X-ray apparatuses 1 is prioritized.

In order to make the best use of current up to the current capacity of a power supply, a current path, on which power is output from the electrical outlet 8 via the external output circuit 50, and a current path on which the battery 12 is charged with power via the charging circuit 60 may be provided, the two current paths may be connected in parallel, and while a current value of an input current is monitored, the two current paths may be current-limited such that the input current does not exceed the current capacity of the power supply source. As a result, since it is possible to simultaneously charge the mobile X-ray apparatuses by making the most of the current capacity of the power supply source, it is possible to complete the charging in a short period of time compared to that in a case where the multiple mobile X-ray apparatuses 1 are to be charged in order one by one.

In order not to exceed the current capacity of the power supply source, while a current value of an input current is monitored, the two current paths may be current-limited such that the input current does not exceed the current capacity of the power supply source. As a result, it is possible to safely charge the mobile X-ray apparatuses without experiencing troubles such as heat generation from the supply source or the turning on of a current breaker.

Figure 3:
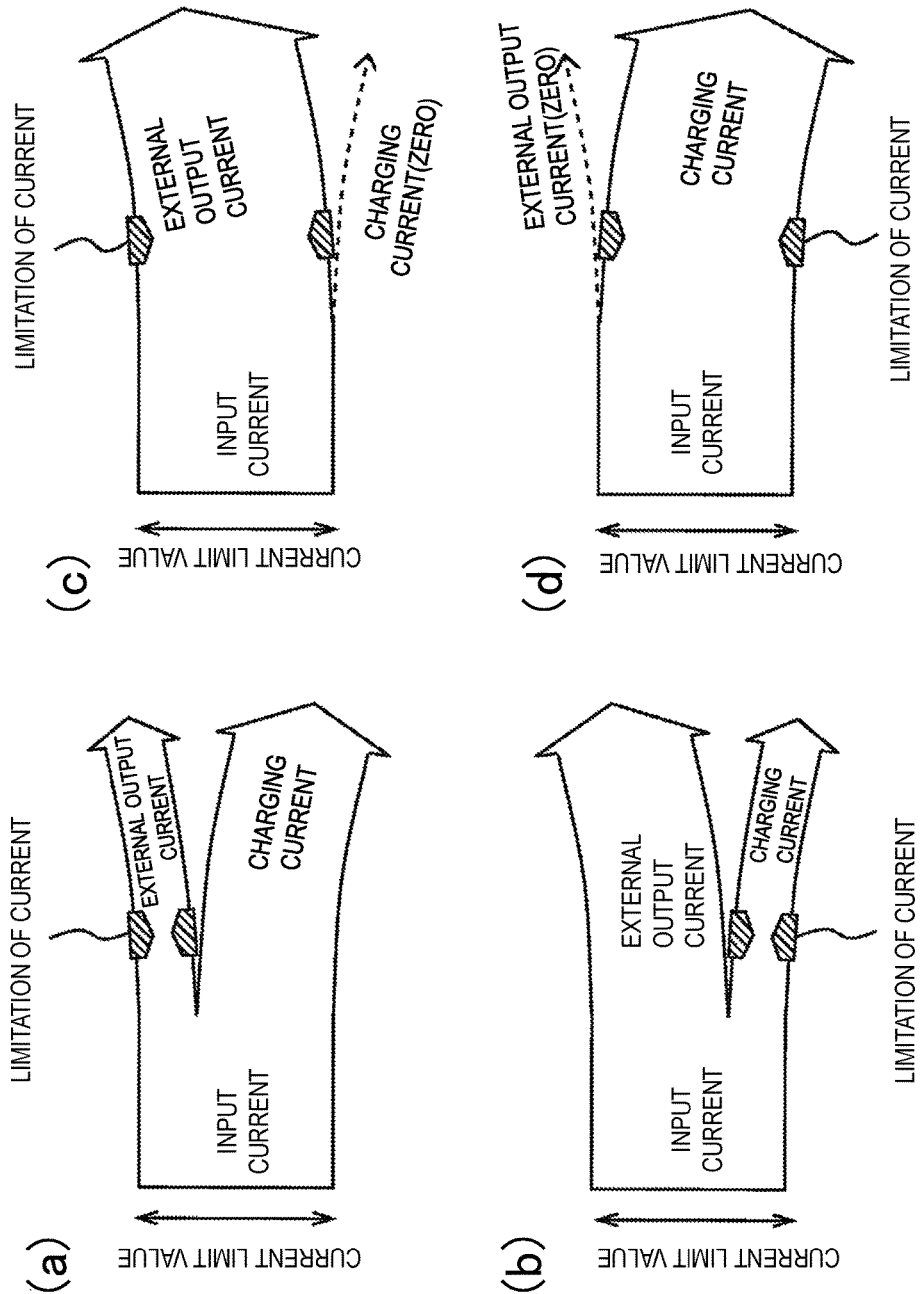
FIG. 3 is a schematic diagram illustrating the distribution of an input current and the limitation of current.

In the invention, since the charging of the connected mobile X-ray apparatuses 1 is prioritized, only one current path in the power supply circuit 30 is current-limited. A priority, in a case where only one of the two current paths is current-limited, will be described with reference to FIG. 3. FIG. 3 schematically illustrates a situation in which an input current of the current limit value is divided into an external output current and a charging current.

In FIG. 3(a), the external output current is limited, and it is possible to increase the charging current by decreasing the external output current. In contrast, in FIG. 3(b), the charging current is limited, and it is possible to increase the external output current by decreasing the charging current. That is, since the two current paths are connected in parallel, current is allowed to flow preferentially in one path by limiting the current of the other path.

Accordingly, in the power supply circuit 30, i) if an external output circuit 50 side is current-limited, since current flows preferentially to a charging circuit 60 side, the battery 12 is preferentially charged, and ii) if the charging circuit 60 side is current-limited, since current flows preferentially to the external output circuit 50 side, power is output preferentially to the electrical outlet 8.

If in the power supply circuit 30, the current of one current path is limited such that the current capacity is not exceeded, and a large amount of current is allowed to flow preferentially in the other current path, it is possible to quickly and safely perform charging in a preferential manner.

If the one current path is current-limited, the entire input current becomes limited, and it is not necessary to detect or limit current flowing in the other current path. As a result, it is possible to limit the input current with a simple circuit configuration.

(1.6 Charging Priority in a Case Where Mobile X-ray Apparatuses 1 are Connected to Each Other)

If the mobile X-ray apparatuses 1 including the power supply circuits 30 in i) or ii) are connected to each other, i) in a case where the external output circuit 50 side is current-limited (refer to FIG. 3(a)), an upstream mobile X-ray apparatus 1a (one close to a wall electrical outlet) of the mobile X-ray apparatuses 1 connected in series is preferentially charged. That is, the closer a mobile X-ray apparatus is positioned to the upstream side, the higher charging priority the mobile X-ray apparatus has. At this time, the (external output current) supplied from the mobile X-ray apparatus 1a to a downstream mobile X-ray apparatus 1b (one positioned away from the wall electrical outlet) becomes equal to the (input current) minus the (charging current). In a case where the external output current is shut off due to the limitation of current, the entire input current becomes the charging current.

ii) For example, in a case where the charging circuit 60 side is current-limited (refer to FIG. 3(b)), current is supplied preferentially to a downstream mobile X-ray apparatus, and thus, a most downstream mobile X-ray apparatus 1c is preferentially charged. That is, the closer a mobile X-ray apparatus is positioned to the downstream side, the higher charging priority the mobile X-ray apparatus has. At this time, the (charging current) supplied to the charging circuit 60 becomes equal to the (input current) minus the (external output current). In a case where the charging current is shut off due to the limitation of current, the entire input current becomes the external output current, and charging is not performed.

In a case where the battery 12 is fully charged (or charging stops), in the power supply circuit 30 in which the external output circuit 50 side is current-limited, the charging current becomes zero, and thus, the entire input current becomes the external output current (refer to FIG. 3(*c*)).

In a case where all the downstream mobile X-ray apparatuses are fully charged (or charging stops), in the power supply circuit 30 in which the charging circuit 60 side is current-limited, the external output current becomes zero, and thus, the entire input current is capable of becoming the charging current (refer to FIG. 3(*d*)).

Since the amount of current supplied from the electrical outlet 8 of the mobile X-ray apparatus 1*a* to the downstream mobile X-ray apparatuses is dependent on the amount of power consumed by the downstream mobile X-ray apparatuses, if power is not consumed by the downstream mobile X-ray apparatuses or the mobile X-ray apparatuses are not connected to the downstream side thereof, regardless of which of the external output circuit 50 side and the charging circuit 60 side is current-limited by the power limiting circuit 40, current supplied from the mobile X-ray apparatus 1*a* to external equipment becomes zero.

Hereinafter, specifically, power supply devices 10, 200, 300, 400, and 500, each using the power supply circuit 30 and the control unit 20, will be described in the first to fifth embodiments.

(2 First Embodiment)

A first embodiment of the mobile X-ray apparatus 1 of the invention will be described. In the embodiment, a user can suitably charge the mobile X-ray apparatuses 1 in the order of the completion of operation of the mobile X-ray apparatuses 1. In the embodiment, the power supply device 10 of the mobile X-ray apparatus 1 uses the power supply circuit 30 in which the external output circuit 50 side is current-limited.

(2.1 Overview of Power Supply Device 10)

The power supply device 10 of the mobile X-ray apparatus 1 of the invention will be described with reference to FIG. 4.

As described above, the power supply device 10 includes the plug 7; the electrical outlet 8; the battery 12; the control unit 20; the current detector 26; and the power supply circuit 30.

In the embodiment, the input and output unit 9 displays the charged state of the mobile X-ray apparatus 1. In the embodiment, among the functional configuration elements of the control unit 20, the limit value acquisition unit 23 and the power limit signal unit 24 are used.

In the power supply circuit 30, the plug 7 is connected to the rectifier circuit 31. An output of the rectifier circuit 31 diverges to the external output circuit 50 side and the charging circuit 60 side, and the external output circuit 50 and the charging circuit 60 are connected in parallel. The power limiting circuit 40 is connected between the rectifier circuit 31 and the external output circuit 50.

(2.2 Operation of Semiconductor Switch 32 and Charging Priority)

The switch drive signal 25 is supplied from the power limit signal unit 24 of the control unit 20 to the semiconductor switch 32 of the power limiting circuit 40.

If the semiconductor switch 32 is turned off by the switch drive signal 25, the current path is shut off, and thus, the external output current does not flow. Since the charging circuit 60 side is not limited, the entire power supplied from the plug 7 flows into the charging circuit 60.

If the semiconductor switch 32 is driven in an on and off manner by the switch drive signal 25, the external output current flows through the external output circuit 50 while being limited, and is output from the electrical outlet 8.

At this time, according to a current limit value acquired by the limit value acquisition unit 23 of the control unit 20, the power limit signal unit 24 adjusts and outputs the switch drive signal 25 such that the input current detected by the current detector 26 does not exceed the current limit value. As a result, it is possible to supply power from the electrical outlet 8 to downstream mobile X-ray apparatuses while supplying power, which is required to charge, to the charging circuit 60. The sum of the power supplied to the charging circuit 60 and the power supplied to the downstream mobile X-ray apparatuses does not exceed the electric capacity of the plug 7.

Accordingly, in a case where the multiple mobile X-ray apparatuses 1 of the embodiment are connected to each other and are charged, the power supply device 10 serves to preferentially charge upstream mobile X-ray apparatuses.

(2.3 Flow of Process Performed by Control Unit 20)

Figure 6:
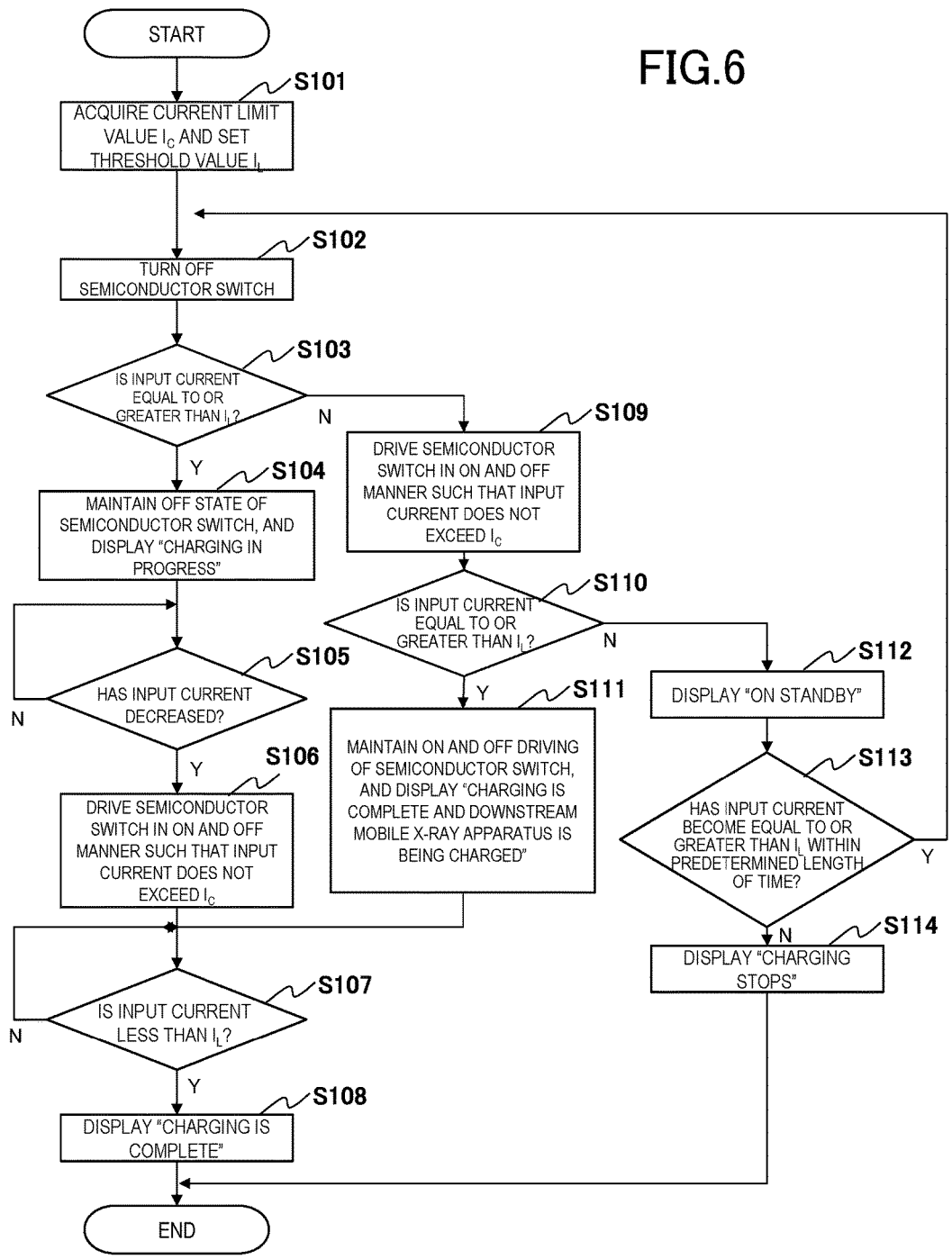
FIG. 6 is a flowchart illustrating a process performed by a control unit 20.

The flow of a process performed by the control unit 20 will be described with reference to a flowchart in FIG. 6.

Prior to charging, a user connects the plug 7 to the electrical outlet 8 of another mobile X-ray apparatus or a wall electrical outlet 13. Thereafter, the control unit 20 controls charging.

First, the limit value acquisition unit 23 of the control unit 20 acquires a current limit value $I_C$ from the storage unit (not illustrated), and sets a threshold value $I_L$ from this value (Step S101).

The threshold value $I_L$ is a reference value at which the control unit 20 performs the switching of the process. For example, in a case where the current limit value $I_C$ is 15 [A] which is a current limit value of a commercial power supply, the threshold value $I_L$ is set to 0.3 [A] which is 2% of $I_C$.

Subsequently, the power limit signal unit 24 of the control unit 20 shuts off current supply to the external output circuit 50 by turning off the semiconductor switch 32 (Step S102). In a case where the input current detected by the current detector 26 is the threshold value $I_L$ or greater (Y in Step S103), the entire input current is supplied to the charging circuit 60, and the battery 12 is charged. The control unit 20 maintains an off state of the semiconductor switch 32, and displays "charging in progress" on the input and output unit 9 (Step S104).

If the charging of the battery 12 proceeds, and the charging current decreases, the input current also decreases. The input current is capable of increasing up to the limit current value $I_C$, and an increased amount of the input current can be supplied to the external output circuit 50. If the current detector 26 detects a decrease in input current (Y in Step S105), the power limit signal unit 24 of the control unit 20 drives the semiconductor switch 32 in an on and off manner (Step S106). Due to the driving of the semiconductor switch 32 in an on and off manner, the external output current starts to flow while being limited. At this time, the power limit signal unit 24 generates and outputs the switch drive signal 25 in which the turn-on time and the turn-off time of the semiconductor switch 32 are adjusted such that the input current detected by the current detector 26 does not exceed the current limit value $I_C$.

Since the external output current is dependent on the amount of power consumed by downstream mobile X-ray apparatuses, in a case where power is not consumed by the downstream mobile X-ray apparatuses or the mobile X-ray apparatuses are not connected to the downstream side thereof, even if the semiconductor switch 32 is driven in an on and off manner, the external output current becomes zero.

Even if the semiconductor switch 32 is repeatedly driven in an on and off manner, the charging current is continuously supplied to the battery 12 via the charging circuit 60.

In a case where the charging further proceeds, and the input current becomes less than the threshold value $I_L$ (Y in Step S107), both the external output current and the charging current are very low. Accordingly, the control unit 20 displays "charging is complete" on the input and output unit 9 (Step S108), and the process is complete.

In a case where the input current is less than $I_L$ in Step S103 (N in Step S103), the input current is very low. This state occurs (i) in a case where current from the upstream side of the plug 7 is shut off, or (ii) in a case where the charging current does not flow due to the battery 12 being fully charged. The power limit signal unit 24 of the control unit 20 drives the semiconductor switch 32 in an on and off manner (Step S109). At this time, the power limit signal unit 24 generates and outputs the switch drive signal 25 in which the turn-on time and the turn-off time of the semiconductor switch 32 are adjusted such that the input current detected by the current detector 26 does not exceed the current limit value $I_C$.

If the input current equal to or greater than $I_L$ flows due to the driving of the semiconductor switch 32 in an on and off manner (Y in Step S110), current is supplied from the upstream side, and since the battery 12 is fully charged, the entire input current is supplied to the external output circuit 50. This implies that power is consumed by the mobile X-ray apparatuses connected to the downstream side thereof. Accordingly, the control unit 20 displays "charging is complete, and charging of downstream X-ray apparatuses is in progress" on the input and output unit 9 (Step S111).

If the input current is less than $I_L$ in Step S110 (N in Step S110), (i) the supply of current to the downstream mobile X-ray apparatuses is shut off due to the charging of an upstream mobile X-ray apparatus in progress or stopping, or (ii) the mobile X-ray apparatus 1 does not require current due to the battery 12 being fully charged and power not being consumed by the downstream mobile X-ray apparatuses (also including a case in which there is no power consumption because the mobile X-ray apparatuses are connected to the downstream side). In this case, since charging is not performed, the control unit 20 displays "on standby" on the input and output unit 9 (Step S112).

In a case where the input current starts to flow in a predetermined length of time thereafter and becomes greater than $I_L$ (Y in Step S113), it is implied that the supply of current from the upstream side to the mobile X-ray apparatus 1 is started. Accordingly, the control unit 20 performs the process from Step S102.

If the input current does not become $I_L$ or greater in the predetermined length of time in Step S113 (N in Step S113), (i) current is not supplied to the mobile X-ray apparatus 1 due to reasons such as a malfunction of the upstream mobile X-ray apparatus, or (ii) current does not flow in the mobile X-ray apparatus 1 and the downstream mobile X-ray apparatuses due to a fully charged state or a malfunction thereof. Accordingly, the control unit 20 displays "charging stops" on the input and output unit 9 (Step S114), and completes the process. The predetermined length of time is desirably set to the length of time taken to fully charge the upstream mobile X-ray apparatus.

The control unit 20 may detect whether the input current becomes less than a predetermined current value instead of detecting a decrease in input current in Step S105. The control unit 20 may display "charging is complete" on the input and output unit 9 after a predetermined length of time has elapsed from when the current detector 26 has detected a decrease in input current in Step S105. The predetermined length of time is desirably set to the length of time taken from a decrease in charging current to a fully charged state.

A voltage detector or the like may be provided, and the control unit 20 may detect whether the plug 7 is connected to and pulled out from the wall electrical outlet 13 or the electrical outlet 8 of the upstream mobile X-ray apparatus, and may start and complete the process.

As illustrated in FIGS. 21(*a*) to 21(*c*), the control unit 20 displays charging statuses such as "on standby", "charging in progress" and "charging is complete" on the input and output unit 9. The input and output unit 9 may display the status of the other connected mobile X-ray apparatuses in addition to the charging status.

(2.4 Change in Input Current in Case Where Three Apparatuses are Connected to Each Other)

Figure 7:
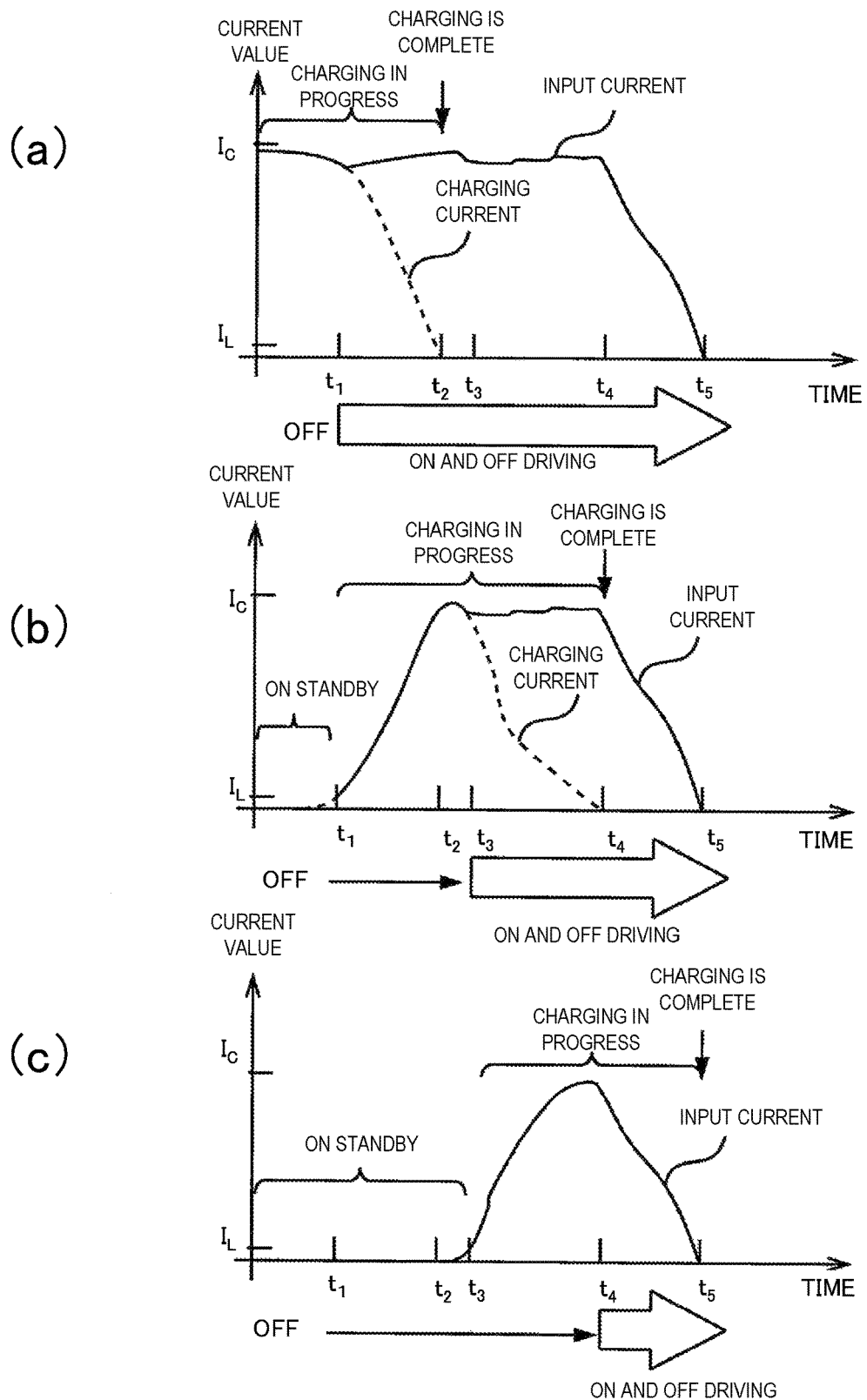
FIG. 7 shows graphs illustrating a change in input current in a case where three mobile X-ray apparatuses 1 are connected to each other.

As described above, the mobile X-ray apparatus 1 is charged. A case in which three mobile X-ray apparatuses 1 requiring charging are connected to each other will be specifically described with reference to FIG. 7. FIGS. 7(*a*) to 7(*c*) are graphs illustrating examples of a change in input current detected by the current detector 26 of each mobile X-ray apparatus in a case where three mobile X-ray apparatuses 1*a*, 1*b*, and 1*c* are connected to each other.

Figure 8:
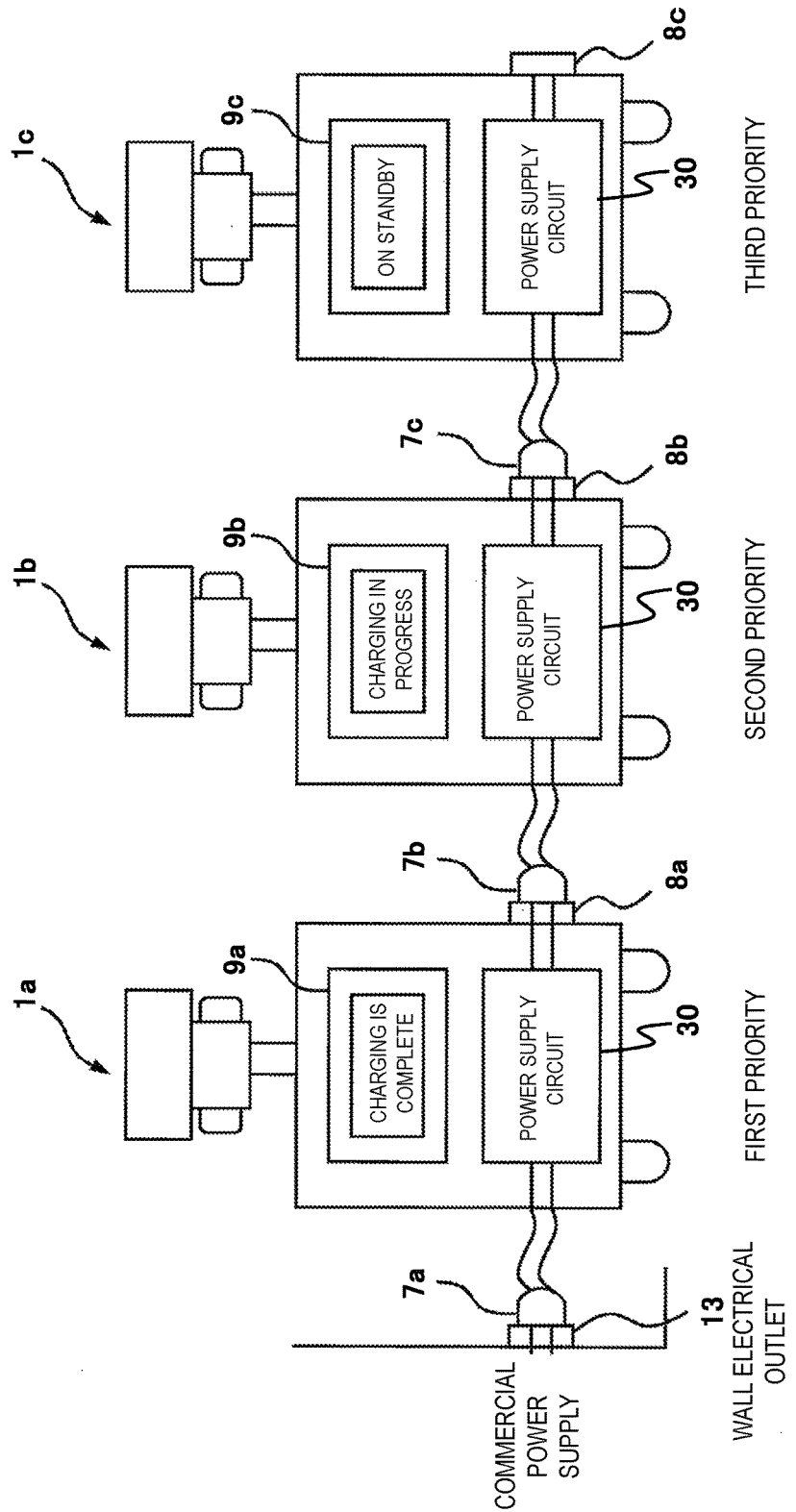
FIG. 8 is a schematic view illustrating the connected three mobile X-ray apparatuses 1.

In a case where the mobile X-ray apparatuses 1 of the embodiment are connected to each other, the closer the mobile X-ray apparatus 1 is positioned to the wall electrical outlet 13, that is, the closer the mobile X-ray apparatus 1 is positioned to the upstream side, the higher charging priority the mobile X-ray apparatus 1 has. The mobile X-ray apparatuses 1*a*, 1*b*, and 1*c* respectively have a first priority, a second priority, and a third priority (refer to FIG. 8).

The mobile X-ray apparatuses 1 will be described in order starting with the mobile X-ray apparatus 1*a* having a first priority.

(2.4.1 Mobile X-ray Apparatus 1*a* and FIG. 7(*a*))

The mobile X-ray apparatus 1*a* has a first charging priority. The mobile X-ray apparatus 1*a* is connected to a most upstream side, and an output from an electrical outlet 8*a* is input to the mobile X-ray apparatus 1*b*. Accordingly, the input current of the mobile X-ray apparatus 1*a* is the sum of the charging current of the mobile X-ray apparatus 1*a* and an output current to the mobile X-ray apparatus 1*b*.

When the semiconductor switch 32 is turned off (Step S102), the external output current is shut off, and thus, the input current of the mobile X-ray apparatus 1*a* is the same as the charging current on the graph (since there is actually slight power consumption inside and outside the power supply circuit, the charging current is slightly lower than the input current; however, for the sake of simplicity, a difference is ignored herein).

At this time, the entire input current equal to or greater than the threshold value $I_L$ flows as the charging current (Y in Step S103), and the charging status becomes "charging in progress" (Step S104).

If the charging of the mobile X-ray apparatus 1*a* proceeds, and the charging current of the mobile X-ray apparatus 1*a* decreases (time $t_1$), the semiconductor switch 32 is driven in an on and off manner (Step S106). Since the semiconductor switch 32 is driven in an on and off manner from time $t_1$, the external output current increases while being limited. In contrast, the input current does not exceed the current limit value $I_C$ due to control being performed by the control unit 20.

The battery 12 becomes fully charged at time $t_2$. The entire input current becomes the external output current after $t_2$ at which a fully charged state is reached. Since the charging of the most downstream mobile X-ray apparatus 1c is complete at time $t_5$, the output current becomes zero, and the input current of the mobile X-ray apparatus 1a also becomes zero (Y in Step S107), and the charging status becomes "charging is complete" (Step S108).

(2.4.2 Mobile X-ray Apparatus 1b: Second Priority and FIG. 7(b))

The mobile X-ray apparatus 1b has a second charging priority. An output of an electrical outlet 8b of the mobile X-ray apparatus 1b is input to a plug 7c of the mobile X-ray apparatus 1c. Accordingly, the input current of the mobile X-ray apparatus 1b on the graph is the sum of the charging current of the mobile X-ray apparatus 1b and an output current to the mobile X-ray apparatus 1c.

Since the input current of the mobile X-ray apparatus 1b is zero until time $t_1$ at which the upstream mobile X-ray apparatus 1a starts to output power to the downstream side, the mobile X-ray apparatus 1b is "on standby" (from N in Step S103 to Step S112).

The input current increases from time $t_1$ (Y in Step S113 to Y in Step S103), and the charging status becomes "charging in progress" (Step S104). The semiconductor switch 32 is driven in an on and off manner from time $t_3$ at which the charging current of the mobile X-ray apparatus 1b starts to decrease (Y in Step S105 to Step S106).

Since the semiconductor switch 32 is driven in an on and off manner from time $t_3$, the external output current increases while being limited. In contrast, the input current does not exceed the current limit value $I_C$ c due to control being performed by the control unit 20.

The battery 12 becomes fully charged at time $t_4$ (Step S108). The entire input current becomes the external output current after $t_4$ at which a fully charged state is reached, and is output to the downstream mobile X-ray apparatus 1c.

(2.4.3 Mobile X-ray Apparatus 1c: Third Priority and FIG. 7(c))

The mobile X-ray apparatus 1c has a third charging priority. Since the mobile X-ray apparatus 1c is connected to a most downstream side, and there is no output from an electrical outlet 8c, the input current of the mobile X-ray apparatus 1c is the same as the charging current on the graph.

Since the input current of the mobile X-ray apparatus 1c is zero until time $t_3$ at which the upstream mobile X-ray apparatus 1b starts to output power to the downstream side, the mobile X-ray apparatus 1c is "on standby" (N in Step S103 to Step S112).

The input current increases from time $t_3$ (Y in Step S113 to Y in Step S103), and the charging status becomes "charging in progress" (Step S104). The semiconductor switch 32 is driven in an on and off manner at time $t_4$ (Step S105 and Step S106). In contrast, even the semiconductor switch 32 is driven in an on and off manner, there is no output to the downstream mobile X-ray apparatus, and thus, the entire input current becomes the charging current.

The charging proceeds, and the battery 12 becomes fully charged at time $t_5$ (Step S108).

(2.5 Effects of Connection Charging)

As described above, in a case where the multiple mobile X-ray apparatuses 1a, 1b, and 1c are connected to each other via the power supply devices 10, it is possible to safely perform charging while making the most of current up to the current capacity of the one wall electrical outlet 13, and it is possible to preferentially charge the mobile X-ray apparatus 1a.

Since the charging of the mobile X-ray apparatus 1a proceeds, and the amount of power required to charge the mobile X-ray apparatus 1a decreases, current, with which the mobile X-ray apparatus 1b can be charged, increases. Since an output from the mobile X-ray apparatus 1a to the mobile X-ray apparatus 1b is limited, the charging time of the mobile X-ray apparatus 1b becomes longer than that in a case where the mobile X-ray apparatus 1b alone is charged; however, it is possible to safely proceed with the charging while making the most of current up to the current capacity of the one wall electrical outlet 13.

If the charging of the mobile X-ray apparatus 1b further proceeds, and the amount of power required to charge the mobile X-ray apparatus 1b decreases, it is possible to charge a next mobile X-ray apparatus 1c. Accordingly, the closer a mobile X-ray apparatus is positioned to the wall electrical outlet 13, the more preferentially it is possible to proceed with the charging of the mobile X-ray apparatus.

The closer a mobile X-ray apparatus is positioned to the upstream side, the sooner the charging of the mobile X-ray apparatus is started. Accordingly, a user can charge mobile X-ray apparatuses in order by connecting the mobile X-ray apparatus 1a, the operation of which is complete, to the wall electrical outlet 13, connecting a plug 7b of the mobile X-ray apparatus 1b, the operation of which is subsequently complete, to the electrical outlet 8a of the mobile X-ray apparatus 1a, and connecting a plug 7c of the mobile X-ray apparatus 1c, the operation of which is subsequently complete, to the electrical outlet 8b of the preceding mobile X-ray apparatus 1b. If the user connects together the mobile X-ray apparatuses 1 and starts to charge the mobile X-ray apparatuses 1, thereafter, it is not necessary for the user to replace the plugs 7, or to change the connections, and can continuously charge all the mobile X-ray apparatuses. As a result, convenience is improved.

Since it is possible to charge all the mobile X-ray apparatuses using one wall electrical outlet, it is not necessary to prepare a power tap, and convenience is improved. At the same time, it is possible to prevent the occurrence of a trouble such as heat generation or smoke generation which becomes a concern in a case where a power tap is used to exceed the current capacity.

If the plug 7 and the electrical outlet 8 are provided on side surfaces of the main body 2, for example, front and rear surfaces or right and left surfaces which are positioned opposite to each other, it is possible to connect together the mobile X-ray apparatuses 1 in a row via short charging cables. As a result, it is possible to decrease a space for accommodating the cable, and it is possible to decrease the size and weight of the mobile X-ray apparatus 1. Since a route distance of the cable becomes short, the surroundings of the mobile X-ray apparatus 1 are kept neat and tidy during charging, and a user can efficiently perform medical activities in the field.

(2.6 Application Examples)

Figure 9:
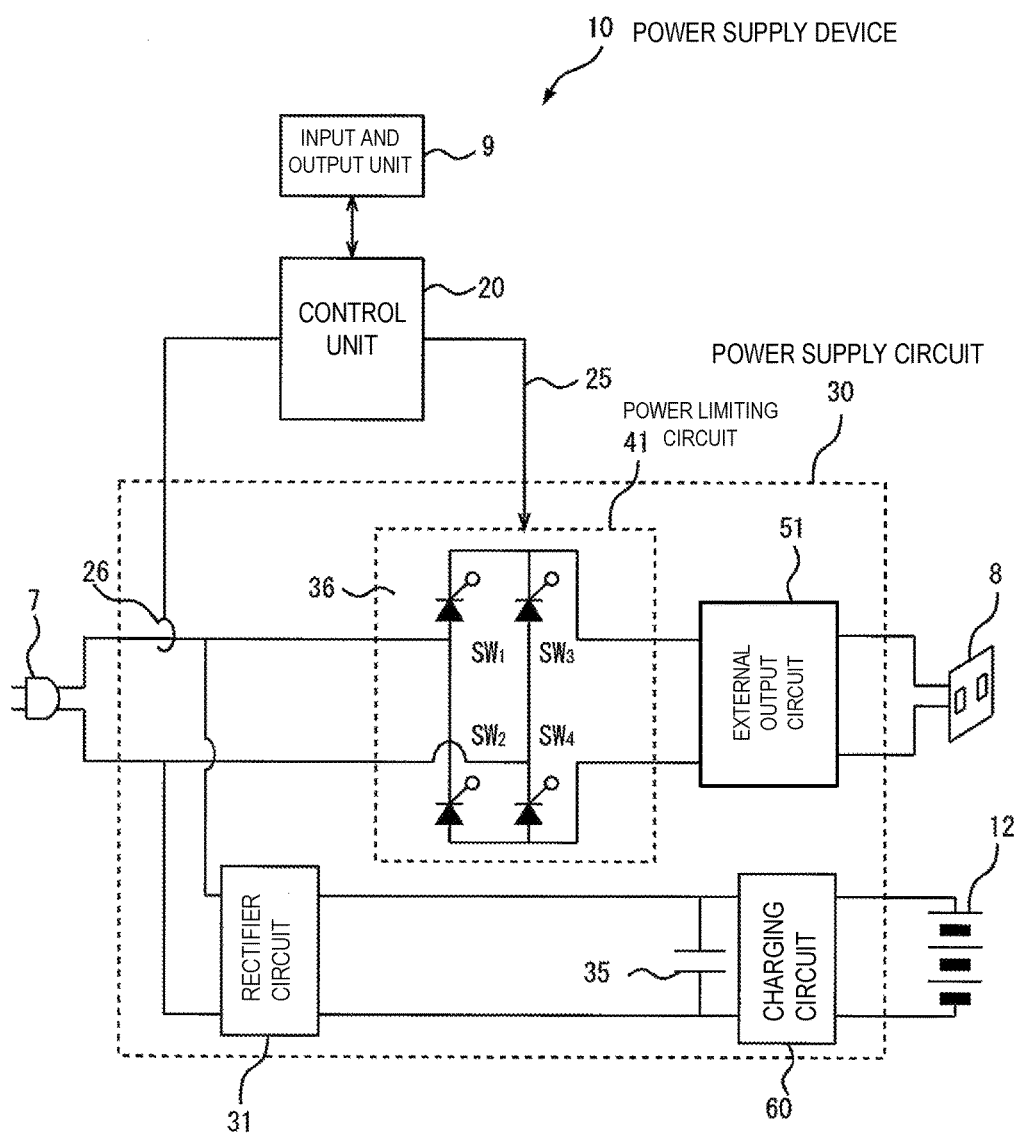
FIG. 9 is a diagram illustrating the function and circuit configuration of the power supply device 10 using a power limiting circuit 41.

A power limiting circuit 41 using a thyristor (semiconductor switch) 36 illustrated in FIG. 9 may be used as a power limiting circuit. The rectifier circuit 31 is connected to the charging circuit 60 side, and the charging circuit 60 is connected to an output side of the rectifier circuit 31. The switch drive signal 25 controls the turn-on times of thyristors $SW_1$ to $SW_4$ such that the input current detected by the current detector 26 becomes equal to the current limit value.

Since an output of the power limiting circuit 41 is alternating current, an inverter circuit is not required. Accordingly, an external output circuit 51 including only a filter circuit illustrated in FIG. 10 may be used. As a result, it is possible to decrease the size and power loss of the power supply device 10.

Figure 10:
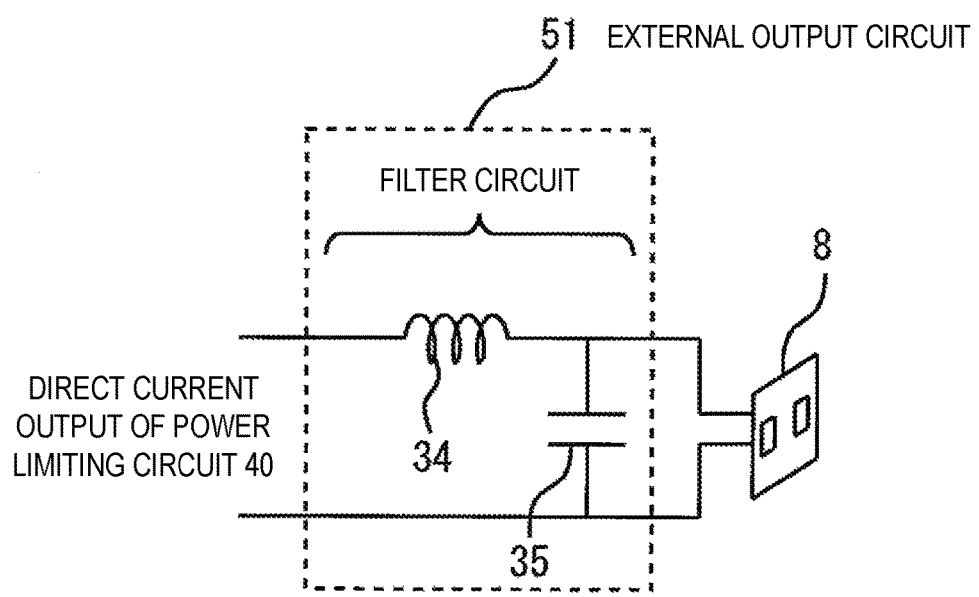
FIG. 10 is a diagram illustrating the circuit configuration of an external output circuit 51.

The external output circuit 51 including only a filter circuit illustrated in FIG. 10 may be also used in a case where direct current is desired to be output from the electrical outlet 8. Since an output of the power limiting circuit 40 (refer to FIG. 4) is direct current, the output is output via the filter circuit. In this case, for the sake of safety, a direct current electrical outlet and a direct current plug are desirably used.

In the embodiment, multiple electrical outlets 8 may be used. Two or more mobile X-ray apparatuses connected to the same mobile X-ray apparatus 1 have the same priority.

If the input and output unit 9 displays a charging priority, a charged state, the length of time taken to the completion of charging, or the like, convenience is more improved (refer to FIG. 21(e)).

In the embodiment, a mobile X-ray apparatus to be connected is the mobile X-ray apparatus of the present invention. In contrast, even if only a mobile X-ray apparatus connected to an end is an apparatus in the related art, it is possible to perform charging in the aforementioned manner.

(2.7 Mobile X-ray Apparatus, Method for Charging Mobile X-ray Apparatus, and Power Supply Device of Embodiment)

In the embodiment, there is provided the mobile X-ray apparatus 1 that takes an X-ray using power charged therein, and includes the power supply device 10 that divides a power, which is input from external equipment (the wall electrical outlet 13 or the electrical outlet 8 of another mobile X-ray apparatus), into at least two powers, outputs one power of the divided powers to the external output circuit 50, 51, outputs the power to external equipment, outputs the other power to the charging circuit 60, and charges the apparatus with the power. The power supply device 10 includes the current detector 26 that detects a current value of the input power; the power limiting circuit 40, 41 that limits the power distributed to the external output circuit 50, 51; and the control unit 20 that controls current flowing in the power limiting circuit 40, 41 based on the current value detected by the current detector 26.

According to the mobile X-ray apparatus 1 of the embodiment, in the power supply circuit 30 inside the power supply device 10, a power input from the external equipment (the wall electrical outlet 13 or the electrical outlet 8 of another mobile X-ray apparatus) is divided into at least two powers, one power of the two powers is distributed to the external output circuit 50, 51 that outputs power to external equipment, and the other power is output to the charging circuit 60 that charges the mobile X-ray apparatus 1 with power. Since the power limiting circuit 40, 41 limits current flowing in the external output circuit 50, 51 based on the current value detected by the current detector 26, it is possible to safely charge the mobile X-ray apparatus 1 without experiencing troubles such as heat generation from a power supply source or the turning on of a current breaker which is caused due to the current exceeding the current capacity of the external power supply.

Desirably, the power limiting circuit 40, 41 is provided in a front stage of the external output circuit 50, 51, and limits current flowing in the external output circuit 50, 51. Accordingly, current flows preferentially to the charging circuit 60 side, and thus, the battery 12 is preferentially charged.

Since charging on the charging circuit 60 side is preferentially performed, if the mobile X-ray apparatuses 1 of the embodiment are connected to each other via the power supply devices 10 and are charged, the upstream mobile X-ray apparatus 1 is preferentially charged. That is, the closer the mobile X-ray apparatus 1 is positioned to the upstream side, the more preferentially it is possible to charge the mobile X-ray apparatus 1.

Desirably, the power limiting circuits 40 and 41 respectively include the semiconductor switches 32 and 36 which increase and decrease the amount of current flowing in a current path. Desirably, the control unit 20 controls the opening and closing of the semiconductor switch 32, 36. Accordingly, the current path is shut off and energized.

Desirably, the power supply device 10 distributes an input current, which is input from external equipment (the wall electrical outlet 13 or the electrical outlet 8 of another mobile X-ray apparatus), to at least two current paths, a first current path of at least the two current paths is connected to the external output circuit 50, 51, and allows an external output current to flow therein, a second current path of at least the two current paths is connected to the charging circuit 60, and allows a charging current to flow therein, the power limiting circuit 40, 41 limits the external output current, the current detector 26 detects a current value of the input current, and the control unit 20 controls the external output current flowing in the power limiting circuit 40, 41 such that the current value of the input current detected by the current detector 26 becomes equal to or less than a current limit value that is the maximum value of current which can be input from the external equipment.

Accordingly, the input current does not exceed the current capacity of the power supply (the wall electrical outlet 13 or the electrical outlet 8 of another mobile X-ray apparatus), and thus, it is possible to safely charge the mobile X-ray apparatus 1 without experiencing troubles such as heat generation from the supply source or the turning on of a current breaker.

In the embodiment, there is provided a method for charging the mobile X-ray apparatus 1 that includes the power supply device 10 which divides a power, which is input from external equipment (the wall electrical outlet 13 or the electrical outlet 8 of another mobile X-ray apparatus), into at least two powers, connects one power of the divided powers to the external output circuit 50, 51, outputs the power to external equipment, connects the other power to the charging circuit 60, and charges the mobile X-ray apparatus 1 with the power, and that takes an X-ray using power charged therein, the method including: a current detection step (Step S105) of detecting a current value of the input power; and a power limitation step (Step S106) of limiting the power output to the external output circuit 50, 51 based on the current value detected in the current detection step.

In the power limitation step (Step S106), the current output to the external output circuit 50, 51 is desirably limited such that the current value detected in the current detection step (Step S105) becomes equal to or less than the current limit value that is the maximum value of current which can be input from the external equipment.

In the embodiment, there is provided the power supply device 10 that divides a power, which is input from external equipment (the wall electrical outlet 13 or the electrical outlet 8 of another mobile X-ray apparatus), into at least two powers, connects one power of the divided powers to the external output circuit 50, 51, outputs the power to external equipment, connects the other power to the charging circuit 60, and charges the mobile X-ray apparatus 1 with the power, the device including: the current detector 26 that detects a current value of the input power, a power limiting circuit 40, 41 that limits the power output to the external output circuit 50, 51, and the control unit 20 that controls current flowing in the power limiting circuit 40, 41 based on the current value detected by the current detector 26.

(3. Second Embodiment)

A second embodiment of the mobile X-ray apparatus 1 of the invention will be described. In the embodiment, a user can suitably complete the charging of the mobile X-ray apparatuses 1 sooner which is positioned away from the wall electrical outlet 13 than other mobile X-ray apparatuses 1. In the embodiment, a power supply device 200 uses the power supply circuit 30 in which the charging circuit 60 side is current-limited.

(3.1 Power Supply Device 200)

Figure 11:
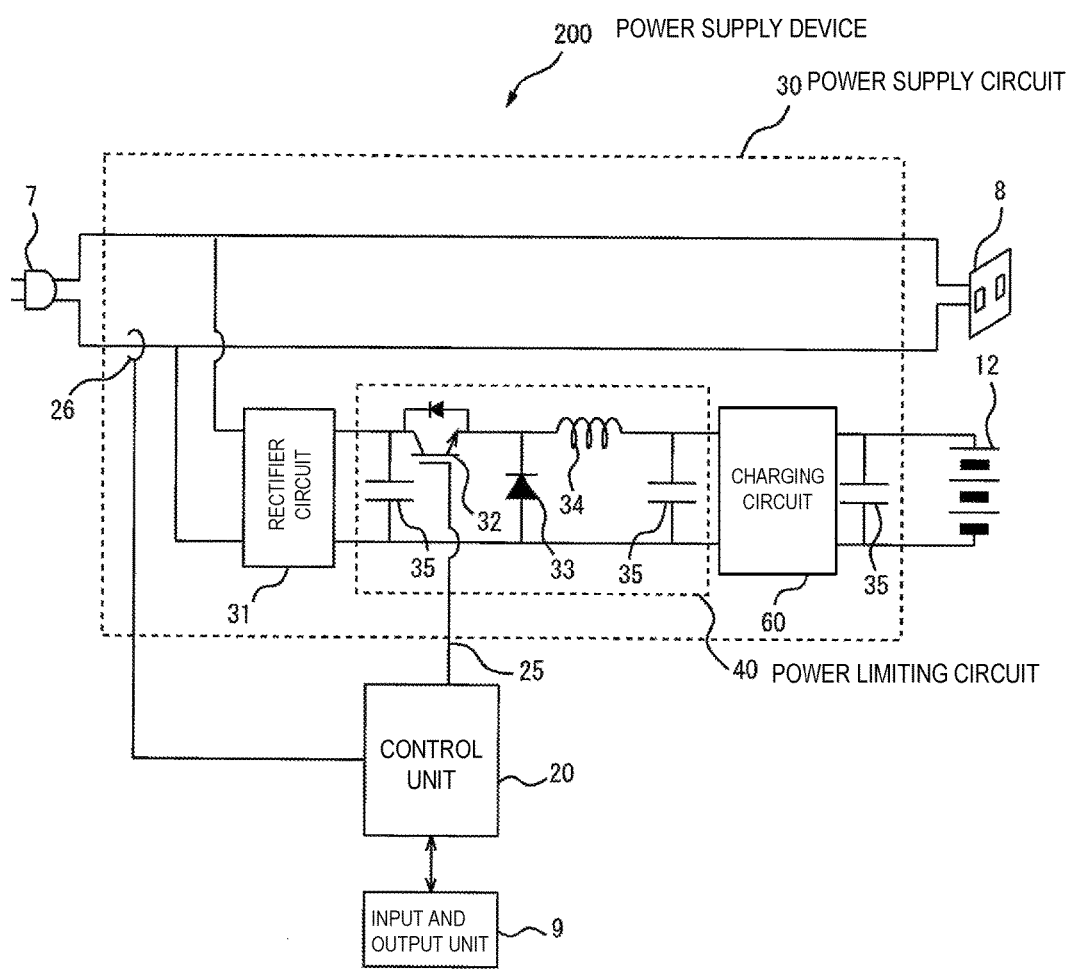
FIG. 11 is a diagram illustrating the function and circuit configuration of a power supply device 200 of a second embodiment.

The power supply device 200 of the mobile X-ray apparatus 1 of the invention will be described with reference to FIG. 11.

Similar to the power supply device of the first embodiment, the power supply device 200 includes the plug 7; the electrical outlet 8; the battery 12; the control unit 20; the current detector 26; and the power supply circuit 30. The power supply circuit 30 of the power supply device 200 has a circuit configuration different from that in the first embodiment.

In the power supply circuit 30 of the embodiment, a back stage of the plug 7 diverges to two paths, that is, an electrical outlet 8 side and the charging circuit 60 side. The electrical outlet 8 is directly connected to the back stage of the plug 7. In contrast, the rectifier circuit 31 of the charging circuit 60 side is connected to the back stage of the plug 7, and the power limiting circuit 40 and the charging circuit 60 are connected to the output side of the rectifier circuit 31.

The power limiting circuit 40 has the same configuration as that in the first embodiment. Also, in the embodiment, among the functional configuration elements of the control unit 20, the limit value acquisition unit 23 and the power limit signal unit 24 are used. The switch drive signal 25 is supplied from the power limit signal unit 24 of the control unit 20 to the semiconductor switch 32 of the power limiting circuit 40.

(3.2 Operation of Semiconductor Switch 32 and Priority of External Output)

If the semiconductor switch 32 is turned off by the switch drive signal 25, the current path is shut off, and thus, the charging current does not flow. Since the electrical outlet 8 side is not limited, current required by downstream mobile X-ray apparatuses is supplied thereto from the plug 7 as an input current, and the entire input current flows into the electrical outlet 8.

If the semiconductor switch 32 is driven in an on and off manner by the switch drive signal 25, the charging current flows through the charging circuit 60 while being limited, and the battery 12 is charged.

At this time, similar to the first embodiment, according to a current limit value acquired by the limit value acquisition unit 23 of the control unit 20, the power limit signal unit 24 adjusts a turn-on/off signal such that the input current detected by the current detector 26 does not exceed the current limit value. As a result, it is possible to supply power to the charging circuit 60 while supplying power required by the downstream mobile X-ray apparatuses. At this time, the sum of the power supplied from the electrical outlet 8 to the downstream mobile X-ray apparatuses and the power supplied to the charging circuit 60 does not exceed the electric capacity of the plug 7.

Accordingly, in a case where multiple mobile X-ray apparatuses 1 of the embodiment are connected to each other and are charged, the power supply device 200 serves to preferentially output power to the mobile X-ray apparatuses connected to the downstream side.

(3.3 Flow of Process Performed by Control Unit 20)

Figure 12:
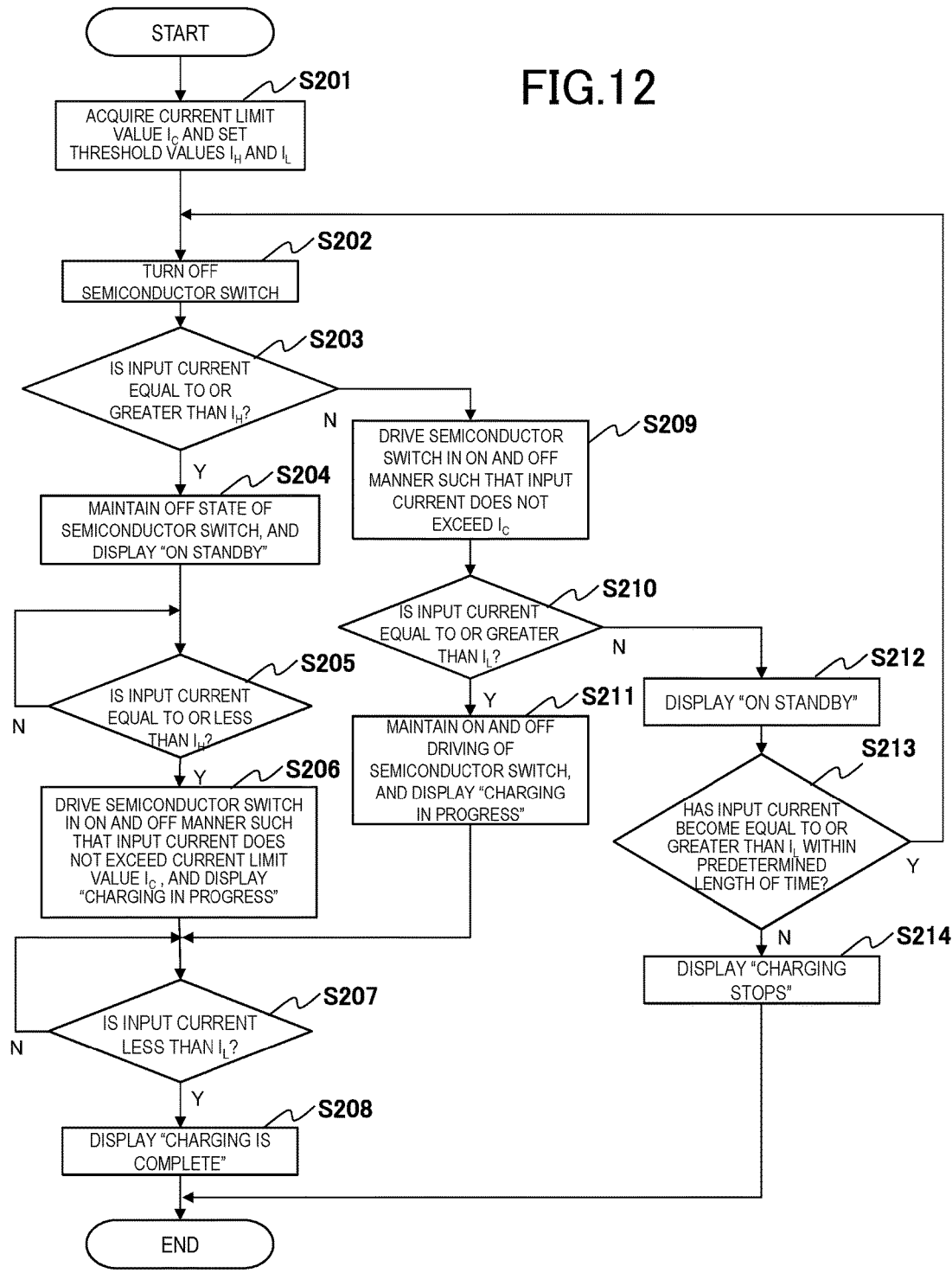
FIG. 12 is a flowchart illustrating a process performed by the control unit 20 of the second embodiment.

The flow of a process performed by the control unit 20 will be described with reference to a flowchart in FIG. 12.

Prior to charging, a user connects the plug 7 to the electrical outlet 8 of another mobile X-ray apparatus or the wall electrical outlet 13. Thereafter, the control unit 20 controls charging.

First, the limit value acquisition unit 23 of the control unit 20 acquires the current limit value $I_C$ from the storage unit (not illustrated), and sets a first threshold value $I_H$ and a second threshold value $I_L$ from this value (Step S201).

The first threshold value $I_H$ and the second threshold value $I_L$ are reference values at which the control unit 20 performs the switching of the process. For example, in a case where the current limit value $I_C$ is 15 [A] which is a current limit value of a commercial power supply, the threshold value $I_H$ is set to 14.7 [A] which is 98% of $I_C$, and the threshold value $I_L$ is set to 0.3 [A] which is 2% of $I_C$.

Subsequently, the power limit signal unit 24 of the control unit 20 turns off the semiconductor switch 32 (Step S202). In a case where the input current detected by the current detector 26 is greater than the threshold value $I_H$ (Y in Step S203), the input current close to the current limit value $I_C$ is supplied to the downstream mobile X-ray apparatuses, and there is no power consumed by the mobile X-ray apparatuses 1. Accordingly, the control unit 20 does not start charging, and displays "on standby" on the input and output unit 9 (Step S204).

If the power consumption of the downstream mobile X-ray apparatuses decreases, the input current also decreases. The input current is capable of increasing up to the current limit value $I_C$, and an increased amount of the input current can be supplied to the charging circuit 60. If the current detector 26 detects that the input current becomes the threshold value $I_H$ or less (Y in Step S205), the power limit signal unit 24 of the control unit 20 drives the semiconductor switch 32 in an on and off manner, and the control unit 20 displays "charging in progress" on the input and output unit 9 (Step S206).

Due to the driving of the semiconductor switch 32 in an on and off manner, the charging current starts to flow while being limited. At this time, the power limit signal unit 24 generates and outputs the switch drive signal 25 in which the turn-on time and the turn-off time of the semiconductor switch 32 are adjusted such that the input current detected by the current detector 26 does not exceed the current limit value $I_C$.

In a case where the charging further proceeds, and the input current becomes less than the threshold value $I_L$ (Y in Step S207), both the external output current and the charging current are very low. Accordingly, the control unit 20 displays "charging is complete" on the input and output unit 9 (Step S208), and the process is complete.

In a case where the input current is less than the threshold value $I_H$ (N in Step S203) and is less than the threshold value $I_L$ (not shown in the drawing) in Step S203, the input current is very low. This state occurs (i) in a case where current from the upstream side of the plug 7 is shut off, or (ii) in a case where power is not consumed by the downstream mobile X-ray apparatuses, or the mobile X-ray apparatuses are not connected to the downstream side. The power limit signal unit 24 of the control unit 20 drives the semiconductor switch 32 in an on and off manner (Step S209). At this time, the power limit signal unit 24 generates and outputs the switch drive signal 25 in which the turn-on time and the turn-off time of the semiconductor switch 32 are adjusted such that the input current detected by the current detector 26 does not exceed the current limit value $I_C$.

If the input current equal to or greater than $I_L$ flows due to the driving of the semiconductor switch 32 in an on and off manner (Y in Step S210), current is supplied from the upstream side, and since power is not consumed by the downstream mobile X-ray apparatuses or the mobile X-ray apparatuses are not connected to the downstream side (state described in (ii)), the entire input current is supplied to the charging circuit 60. Accordingly, the control unit 20 displays "charging in progress" on the input and output unit 9 (Step S211).

If the input current is less than $I_L$ in Step S210 (N in Step S210), (i) the supply of current from the upstream side of the plug 7 to the mobile X-ray apparatus 1 is shut off, or (ii) the mobile X-ray apparatus 1 does not require current due to the battery 12 being fully charged and power not being consumed by the downstream mobile X-ray apparatuses (also including a case in which there is no power consumption because the mobile X-ray apparatuses are not connected to the downstream side). In this case, since charging is not performed, the control unit 20 displays "on standby" on the input and output unit 9 (Step S212).

In a case where the input current starts to flow in a predetermined length of time thereafter and becomes $I_L$ or greater (Y in Step S213), it is implied that the supply of current from the upstream side to the mobile X-ray apparatus 1 is started. Accordingly, the control unit 20 performs the process from Step S202.

If the input current does not become $I_L$ or greater in the predetermined length of time in Step S213 (N in Step S213), (i) current is not supplied to the mobile X-ray apparatus 1 due to reasons such as a malfunction of the upstream mobile X-ray apparatus, or (ii) current does not flow in the mobile X-ray apparatus 1 and the downstream mobile X-ray apparatuses due to a fully charged state or a malfunction thereof. Accordingly, the control unit 20 displays "charging stops" on the input and output unit 9 (Step S112), and completes the process.

(3.4 Change in Input Current in Case Where Three Apparatuses are Connected to Each Other)

Figure 13:
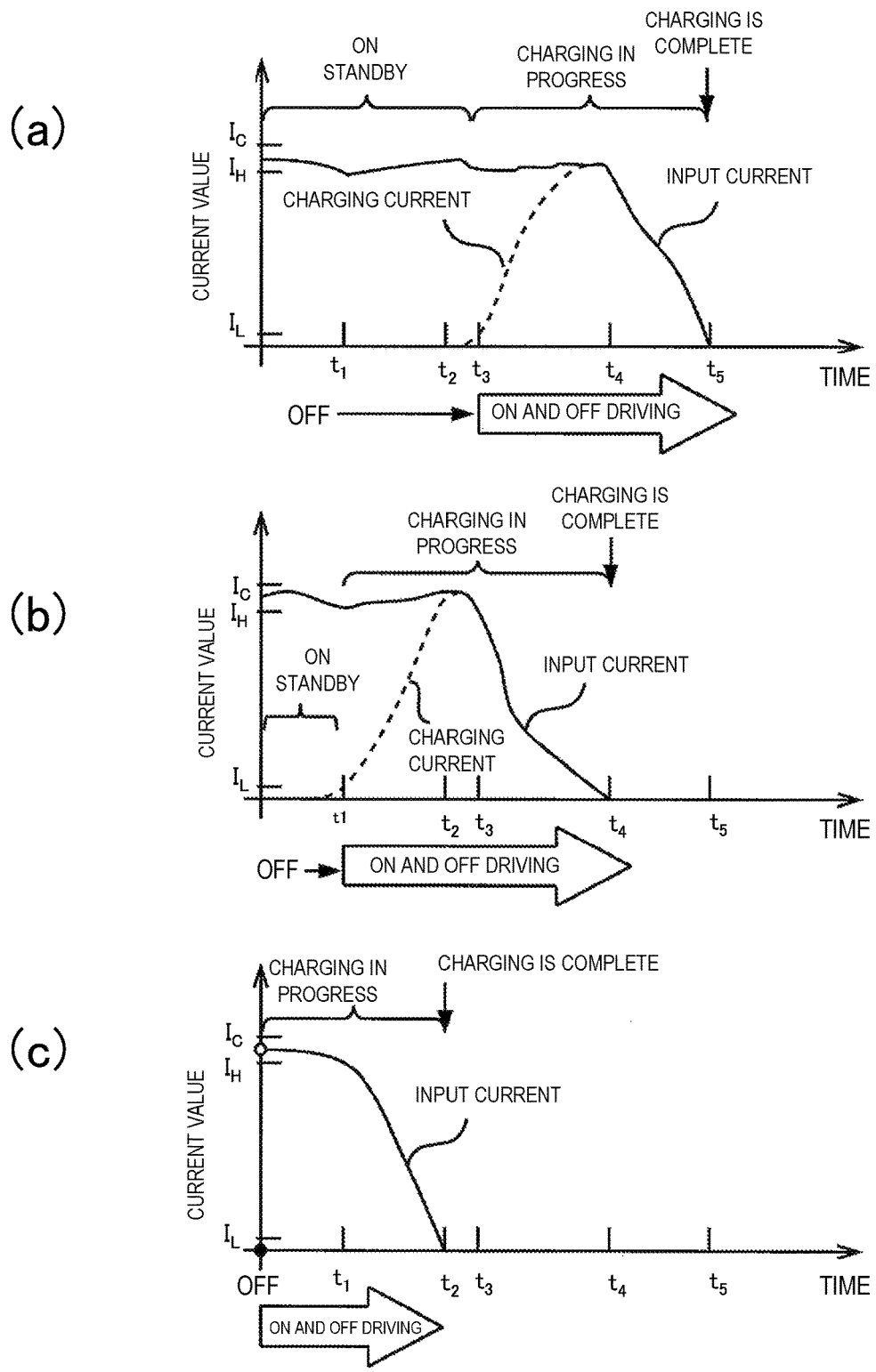
FIG. 13 shows graphs illustrating a change in input current in a case where the three mobile X-ray apparatuses 1 of the second embodiment are connected to each other.

As described above, the mobile X-ray apparatus 1 is charged. A case in which three mobile X-ray apparatuses 1 requiring charging are connected to each other will be specifically described with reference to FIG. 13. FIGS. 13(*a*), (*b*) and (*c*) are graphs illustrating examples of a change in input current detected by the current detector 26 of each mobile X-ray apparatus in a case where the three mobile X-ray apparatuses 1*a*, 1*b*, and 1*c* are connected to each other.

Figure 14:
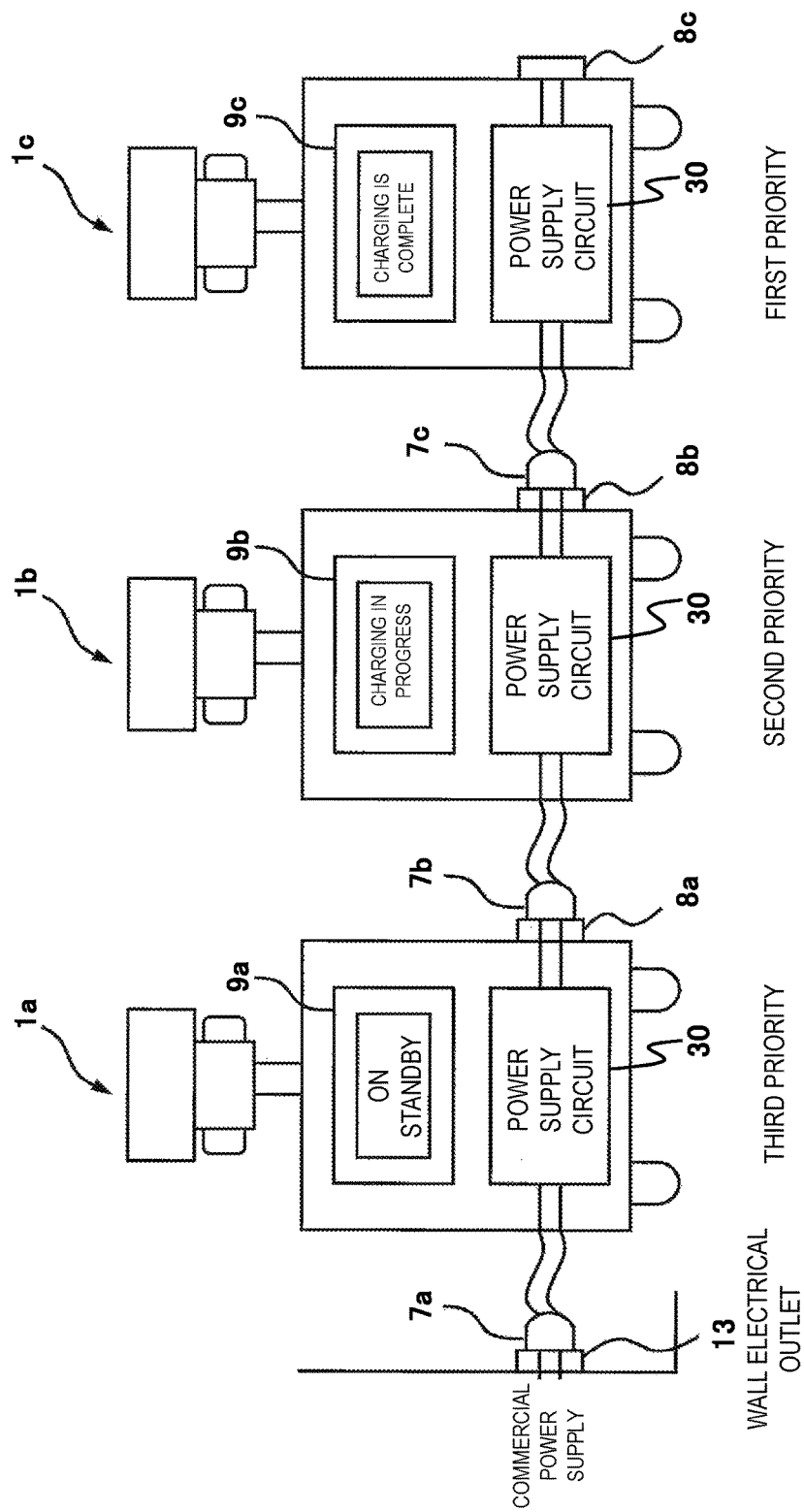
FIG. 14 is a schematic view illustrating the connected three mobile X-ray apparatuses 1 of the second embodiment.

In a case where the mobile X-ray apparatuses 1 of the embodiment are connected to each other, the further the mobile X-ray apparatus 1 is positioned away from the wall electrical outlet 13, that is, the closer the mobile X-ray apparatus 1 is positioned to the downstream side, the higher charging priority the mobile X-ray apparatus 1 has. The mobile X-ray apparatuses 1*a*, 1*b*, and 1*c* respectively have a third priority, a second priority, and a first priority (refer to FIG. 14).

The mobile X-ray apparatuses 1 will be described in order starting with the mobile X-ray apparatus 1*c* having a first priority.

(3.4.1 Mobile X-ray Apparatus 1*c* and FIG. 13(*c*))

The mobile X-ray apparatus 1*c* has a first priority. Since the mobile X-ray apparatus 1*c* is connected to a most downstream side, and there is no output from the electrical outlet 8*c*, the input current of the mobile X-ray apparatus 1*c* is the same as the charging current (since there is actually slight power consumption inside and outside the power supply circuit, the charging current is slightly lower than the input current; however, for the sake of simplicity, a difference is ignored herein).

When the semiconductor switch 32 is turned off (Step S202), the charging current is shut off, and thus, the input current is zero, that is, is less than the threshold value $I_L$ (N in Step S203). Subsequently, if the semiconductor switch 32 is driven in an on and off manner (Step S209), the input current equal to or greater than the threshold value $I_L$ flows (Y in Step S210), charging is started, and the charging status becomes "charging in progress" (Step S211).

If the charging of the mobile X-ray apparatus 1*c* proceeds, and the charging current decreases, the input current detected by the current detector 26 also decreases. If the battery 12 becomes fully charged at time $t_2$, the input current becomes less than the threshold value $I_L$ (Step S207), and the charging status becomes "charging is complete" (Step S208).

(3.4.2 Mobile X-ray Apparatus 1*b* and FIG. 13(*b*))

The mobile X-ray apparatus 1*b* has a second charging priority. An output of the electrical outlet 8*b* of the mobile X-ray apparatus 1*b* is input to the plug 7*c* of the mobile X-ray apparatus 1*c*. Accordingly, the input current of the mobile X-ray apparatus 1*b* on the graph is the sum of the charging current of the mobile X-ray apparatus 1*b* and an output current to the mobile X-ray apparatus 1*c*.

When the semiconductor switch 32 is turned off (Step S202), the charging current is shut off, and thus, the input current represents the output current to the downstream mobile X-ray apparatus 1*c*. Since current equal to or greater than the threshold value $I_H$ is output to the downstream mobile X-ray apparatus 1*c*, the input current of the mobile X-ray apparatus 1*b* is the threshold value $I_H$ or greater (Y in Step S203). Accordingly, the charging status becomes "on standby" (Step S204).

If the charging of the downstream mobile X-ray apparatus 1*c* proceeds, and the external output current starts to decrease, the input current of the mobile X-ray apparatus 1*b* also starts to decrease. If the input current of the mobile X-ray apparatus 1*b* is the threshold value $I_H$ or less at time $t_1$ (Y in Step S205), the semiconductor switch 32 is driven in an on and off manner, and the charging status becomes "charging in progress" (Step S206). Since the semiconductor switch 32 is driven in an on and off manner from time $t_1$, the charging current increases while being limited. In contrast, the input current does not exceed the current limit value $I_C$ due to control being performed by the control unit 20.

Since there is no output to the downstream mobile X-ray apparatus 1*c* after time $t_2$, the entire input current on the graph represents the charging current. Eventually, if the charging of the mobile X-ray apparatus 1*b* proceeds, and the battery 12 becomes fully charged at time $t_4$, the input current value becomes less than the threshold value $I_L$ (Step S207), and the charging status becomes "charging is complete" (Step S208).

(3.4.3 Mobile X-ray Apparatus 1*a* and FIG. 13(*a*))

The mobile X-ray apparatus 1*a* has a third charging priority. An output from the electrical outlet 8*a* of the mobile X-ray apparatus 1*a* is input to the mobile X-ray apparatus 1*b*. Accordingly, the input current of the mobile X-ray apparatus 1*a* on the graph is the sum of an output current to the mobile X-ray apparatus 1b and the charging current of the mobile X-ray apparatus 1a.

When the semiconductor switch 32 is turned off (Step S202), the charging current is shut off, and thus, the input current represents the output current to the downstream mobile X-ray apparatus 1b. Since current equal to or greater than the threshold value $I_L$ is output to the downstream mobile X-ray apparatus 1b, the input current of the mobile X-ray apparatus 1a is the threshold value $I_H$ or greater (Y in Step S203). Accordingly, the charging status becomes "on standby" (Step S204).

If the charging of the downstream mobile X-ray apparatus 1b proceeds, and the external output current starts to decrease, the input current of the mobile X-ray apparatus 1a also starts to decrease. If the input current of the mobile X-ray apparatus 1a is the threshold value $I_H$ or less at time $t_3$ (Y in Step S205), the semiconductor switch 32 is driven in an on and off manner, and the charging status becomes "charging in progress" (Step S206). Since the semiconductor switch 32 is driven in an on and off manner from time $t_3$, the charging current increases while being limited. In contrast, the input current does not exceed the current limit value $I_C$ due to control being performed by the control unit 20.

Since there is no output to the downstream mobile X-ray apparatus 1b after time $t_4$, the entire input current on the graph represents the charging current. Eventually, if the charging of the mobile X-ray apparatus 1a proceeds, and the battery 12 becomes fully charged at time $t_5$, the input current becomes less than the threshold value $I_L$ (Step S207), and the charging status becomes "charging is complete" (Step S208).

(3.4.4 Change in Input Current in Case Where Connection of Mobile X-ray Apparatus 1c is Cut)

Figure 15:
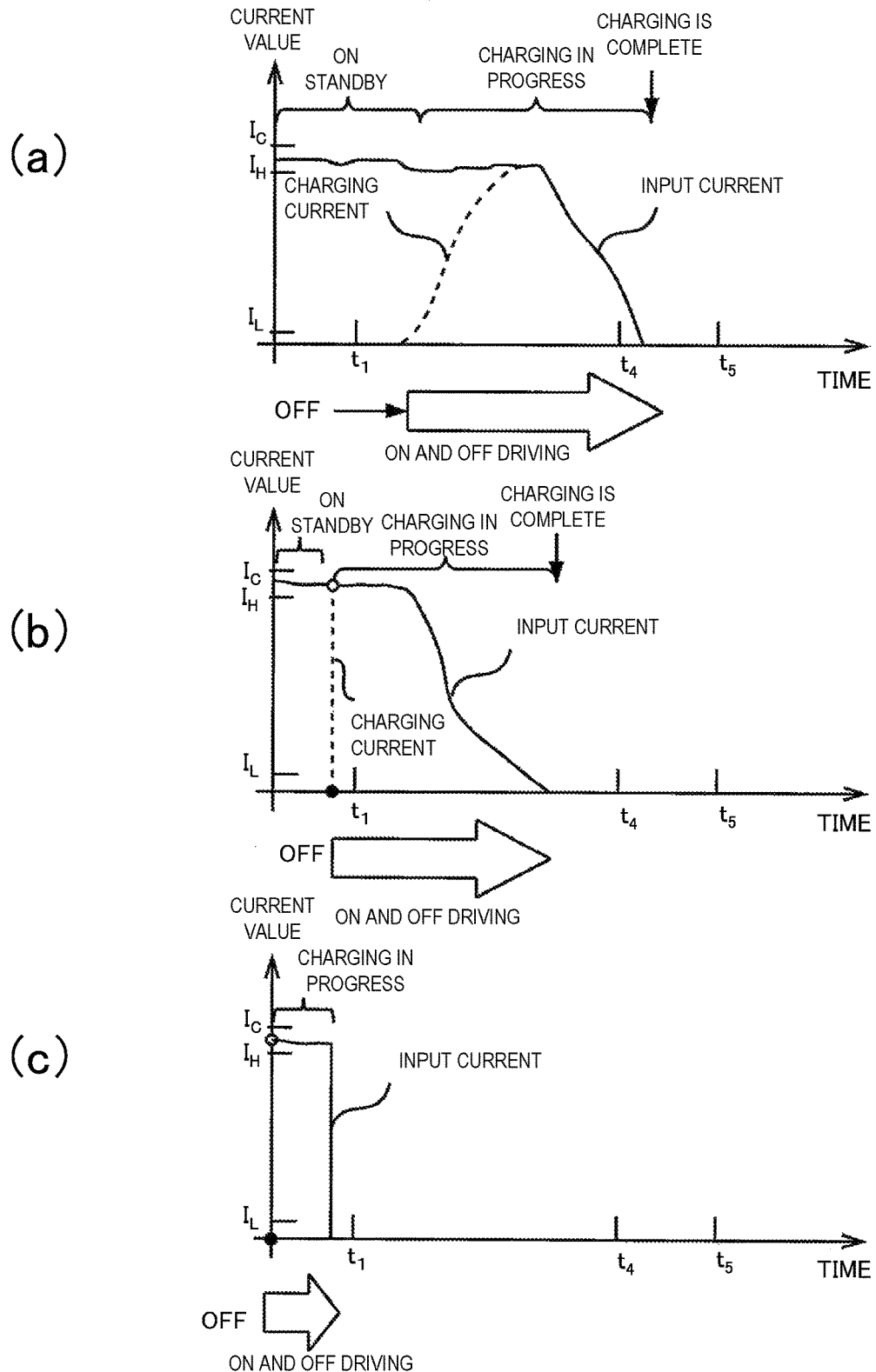
FIG. 15 shows graphs illustrating a change in input current in a case where a plug of a mobile X-ray apparatus re which is being charged is pulled out.

Hereinafter, a case, in which the plug 7c of the most downstream mobile X-ray apparatus 1c is pulled out prior to time $t_1$ during charging, will be described with reference to FIG. 15.

If the plug 7c of the mobile X-ray apparatus 1c is pulled out, naturally, the input current of the mobile X-ray apparatus 1c becomes equal to or less than the threshold value $I_H$ (refer to FIG. 15(c)). Since there is no supply of current from the mobile X-ray apparatus 1b (refer to FIG. 15(b)) to the downstream mobile X-ray apparatus 1c at the same time, the input current of the mobile X-ray apparatus 1b becomes zero (Y in Step S205). The semiconductor switch 32 is driven in an on and off manner, the charging status of the mobile X-ray apparatus 1b "on standby" up to that time becomes "charging in progress" (Step S206). Eventually, if the charging of the mobile X-ray apparatus 1b proceeds, and the battery 12 becomes fully charged, the input current becomes less than the threshold value $I_L$ (Step S207), and the charging status becomes "charging is complete" (Step S208).

In a case where a mobile X-ray apparatus is additionally connected to the downstream side of the most downstream mobile X-ray apparatus 1c, the additional mobile X-ray apparatus is preferentially charged. In this case, if an upstream mobile X-ray apparatus is being charged, the charging of the mobile X-ray apparatus which is being charged stops, and the charging status becomes "on standby". The control unit 20 desirably performs control such that charging is started again after the charging current of the additional mobile X-ray apparatus has decreased.

(3.5 Effects of Connection Charging)

As described above, in a case where the multiple mobile X-ray apparatuses 1a, 1b, and 1c are connected to each other via the power supply devices 10, it is possible to safely perform charging while making the most of current up to the current capacity of the one wall electrical outlet 13. In addition, it is possible to preferentially charge the most downstream mobile X-ray apparatus 1c.

Since the charging of the mobile X-ray apparatus 1c proceeds, and the amount of power required to charge the mobile X-ray apparatus 1c decreases, current, with which the mobile X-ray apparatus 1b can be charged, increases. Since the charging current of the mobile X-ray apparatus 1b is limited, the charging time of the mobile X-ray apparatus 1b becomes longer than that in a case where the mobile X-ray apparatus 1b alone is charged; however, it is possible to safely proceed with the charging while making the most of current up to the current capacity of the one wall electrical outlet 13. In addition, the continuous charging of the multiple mobile X-ray apparatuses can be automatically performed without a user annoyingly using the hand.

If the charging of the mobile X-ray apparatus 1b further proceeds, and the amount of power required to charge the mobile X-ray apparatus 1b decreases, the charging of the mobile X-ray apparatus 1a is automatically started. As such, the further a mobile X-ray apparatus is positioned away from the wall electrical outlet 13, the more preferentially it is possible to proceed with the charging of the mobile X-ray apparatus.

The closer a mobile X-ray apparatus is positioned to the downstream side, the sooner the charging of the mobile X-ray apparatus is complete. Accordingly, first, a user can use a distal mobile X-ray apparatus. For this reason, when the user moves a mobile X-ray apparatus, the charging of which is complete, to a service place, it is not necessary for the user to move the other mobile X-ray apparatuses, or to reconnect the plugs of the other mobile X-ray apparatuses. As a result, the user can smoothly proceed with preparation in going the rounds.

Since a most downstream apparatus, which requires the minimum amount of time and efforts to disconnect a charging cable, is preferentially charged, also in a case where a mobile X-ray apparatus is urgently needed, a user can immediately move and use the most downstream mobile X-ray apparatus 1 without paying attention to the charged state of each mobile X-ray apparatus. As a result, the use of the mobile X-ray apparatus of the embodiment is very convenient.

Even if a distal mobile X-ray apparatus which is being charged is disconnected, since the charging of a mobile X-ray apparatus, which becomes a new distal mobile X-ray apparatus and is positioned on the immediately upstream side of the distal mobile X-ray apparatus, is immediately started, it is possible to obtain a mobile X-ray apparatus soon, the charging of which is subsequently complete, and at this time, it is not necessary for a user to manage the charging. As a result, the use of the mobile X-ray apparatus of the embodiment is very convenient.

Similar to the first embodiment, it is not necessary to prepare a power tap, and it is possible to shorten charging cables. It is possible to decrease a space for accommodating the cable by shortening the charging cable, and it is possible to decrease the size and weight of the mobile X-ray apparatus 1. Since a route distance of the cable becomes short, a user can efficiently perform medical activities in the field.

(3.6 Application Examples)

Figure 16:
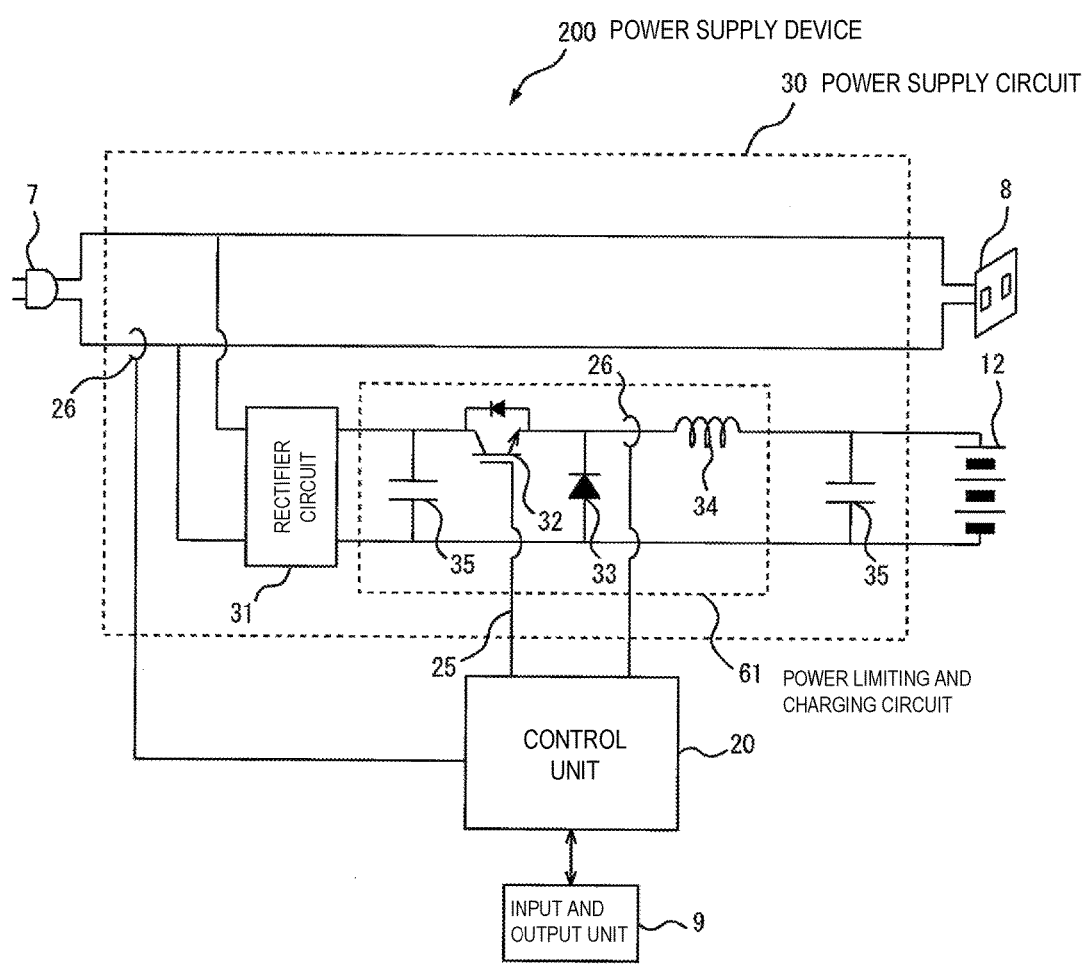
FIG. 16 is a diagram illustrating the function and circuit configuration of the power supply device 200 using a power limiting and charging circuit 61.

As illustrated in FIG. 16, a power limiting and charging circuit 61 which serves as both a power limiting circuit and a charging circuit may be used. The power limiting and charging circuit 61 includes the current detector 26 that detects a charging current. The power limit signal unit 24 of the control unit 20 drives the semiconductor switch 32 in an on and off manner and controls a charging current such that an input current value of the plug 7 does not exceed a current limit value, and the charging current does not exceed an allowable current value of the battery 12.

As a result, it is possible to increase the life span of the battery by reducing the amount of heat generated from the battery. Since the power limiting and charging circuit 61 also serves as a power limiting circuit, it is possible to decrease the size and power loss of the power supply circuit 30.

In the embodiment, the threshold values $I_H$ and $I_L$ are set from the current limit $I_C$, and the control unit 20 switches the process according to the values. Alternatively, the control unit 20 may switch the process according to an increase and decrease in input current value.

(3.7 Mobile X-ray Apparatus, Method for Charging Mobile X-ray Apparatus, and Power Supply Device of Embodiment)

In the embodiment, there is provided the mobile X-ray apparatus 1 that takes an X-ray using power charged therein, and that includes the power supply device 200 that divides a power, which is input from external equipment (the wall electrical outlet 13 or the electrical outlet 8 of another mobile X-ray apparatus), into at least two powers, connects one power of the divided powers to the electrical outlet 8 side, outputs the power to external equipment, connects the other power to the charging circuit 60, and charges the apparatus with the power. The power supply device 200 includes the current detector 26 that detects a current value of the input power; the power limiting circuit 40 that limits power output to the charging circuit 60; and the control unit 20 that controls current flowing in the power limiting circuit 40 based on the current value detected by the current detector 26.

According to the mobile X-ray apparatus 1 of the embodiment, in the power supply circuit 30 inside the power supply device 200, a power input from the external equipment (the wall electrical outlet 13 or the electrical outlet 8 of another mobile X-ray apparatus) is divided into at least two powers, one power of the two powers is distributed to the electrical outlet 8 that outputs power to external equipment, and the other power is output to the charging circuit 60 that charges the mobile X-ray apparatus 1 with power. Since the power limiting circuit 40 limits current flowing in the charging circuit 60 based on the current value detected by the current detector 26, it is possible to safely charge the mobile X-ray apparatus 1 without experiencing troubles such as heat generation from an external power supply source (the wall electrical outlet 13 or the electrical outlet 8 of another mobile X-ray apparatus) or the turning on of a current breaker which is caused due to the current exceeding the current capacity of the external power supply source.

If the amount of current flowing in the charging circuit 60 is limited, the entire input power becomes limited, and it is not necessary to detect or limit current flowing on the electrical outlet 8 side. As a result, it is possible to perform charging with a simple circuit configuration.

Desirably, the power limiting circuit 40 is provided in a front stage of the charging circuit 60 and limits current flowing in the charging circuit 60. Since current flows preferentially to the electrical outlet 8 side, power is output preferentially to the electrical outlet 8, and is output preferentially to external equipment. Accordingly, if the mobile X-ray apparatuses 1 of the embodiment are connected to each other via the power supply devices 200 and are charged, current is supplied preferentially to the downstream mobile X-ray apparatus 1, and the most downstream mobile X-ray apparatus 1c is preferentially charged. That is, the closer the mobile X-ray apparatus 1 is positioned to the downstream side, the more preferentially it is possible to charge the mobile X-ray apparatus 1.

Desirably, the power limiting circuit 40 includes the semiconductor switch 32 which increases and decreases the amount of current flowing in a current path. Desirably, the control unit 20 controls the opening and closing of the semiconductor switch 32. Accordingly, the current path is shut off and energized.

Desirably, the power supply device 200 distributes an input current, which is input from external equipment (the wall electrical outlet 13 or the electrical outlet 8 of another mobile X-ray apparatus), to at least two current paths, a first current path of at least the two current paths is connected to the electrical outlet 8, and allows an external output current to flow therein, a second current path of at least the two current paths is connected to the charging circuit 60, and allows a charging current to flow therein, the power limiting circuit 40 limits the charging current, the current detector 26 detects a current value of the input current, and the control unit 20 controls the charging current flowing in the power limiting circuit 40 such that the current value of the input current detected by the current detector 26 becomes equal to or less than a current limit value that is the maximum value of current which can be input from the external equipment.

Accordingly, the input current does not exceed the current capacity of the power supply source (the wall electrical outlet 13 or the electrical outlet 8 of another mobile X-ray apparatus), and thus, it is possible to safely charge the mobile X-ray apparatus 1 without experiencing troubles such as heat generation from the supply source or the turning on of a current breaker.

In the embodiment, there is provided a method for charging the mobile X-ray apparatus 1 that includes the power supply device 200 which divides a power, which is input from external equipment (the wall electrical outlet 13 or the electrical outlet 8 of another mobile X-ray apparatus), into at least two powers, connects one power of the divided powers to the electrical outlet 8, outputs the power to external equipment, connects the other power to the charging circuit 60, and charges the mobile X-ray apparatus 1 with the power, and that takes an X-ray using power charged therein, the method including: a current detection step (Step S205) of detecting a current value of the input power; and a power limitation step (Step S206) of limiting power output to the charging circuit 60 based on the current value detected in the current detection step.

In the power limitation step (Step S206), the current distributed to the charging circuit 60 is desirably limited such that the current value detected in the current detection step (Step S205) becomes equal to or less than the current limit value that is the maximum value of current which can be input from the external equipment.

In the embodiment, there is provided the power supply device 200 that divides a power, which is input from external equipment (the wall electrical outlet 13 or the electrical outlet 8 of another mobile X-ray apparatus), into at least two powers, connects one power of the divided powers to the electrical outlet 8, outputs the power to external equipment, connects the other power to the charging circuit 60, and charges the mobile X-ray apparatus 1 with the power, the device including: the current detector 26 that detects a current value of the input power, the power limiting circuit 40 that limits power output to the charging circuit 60, and the control unit 20 that controls current flowing in the power limiting circuit 40 based on the current value detected by the current detector 26.

(4 Third Embodiment)

A third embodiment of the mobile X-ray apparatus 1 of the invention will be described. In the embodiment, a user can suitably define priorities of the mobile X-ray apparatuses 1, and charge the mobile X-ray apparatuses 1. A power supply device 300 of the embodiment has the function of communicating with power supply devices inside other mobile X-ray apparatuses, and setting a charging priority.

(4.1 Power Supply Device 300)

Figure 17:
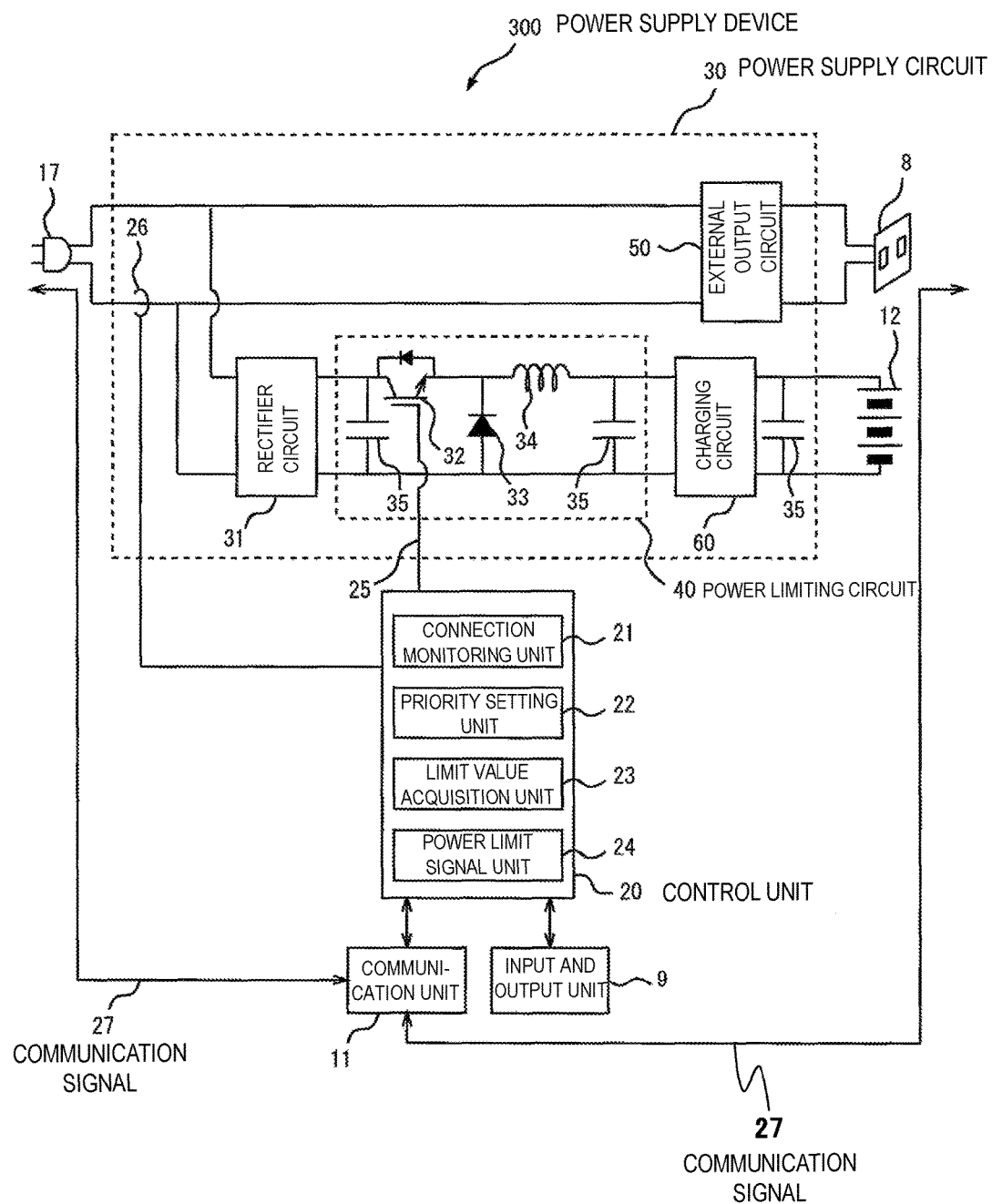
FIG. 17 is a diagram illustrating the function and circuit configuration of a power supply device 300 of a third embodiment.

FIG. 17 illustrates the power supply device 300. The power supply device 300 of the mobile X-ray apparatus 1 of the invention will be described.

Figure 18:
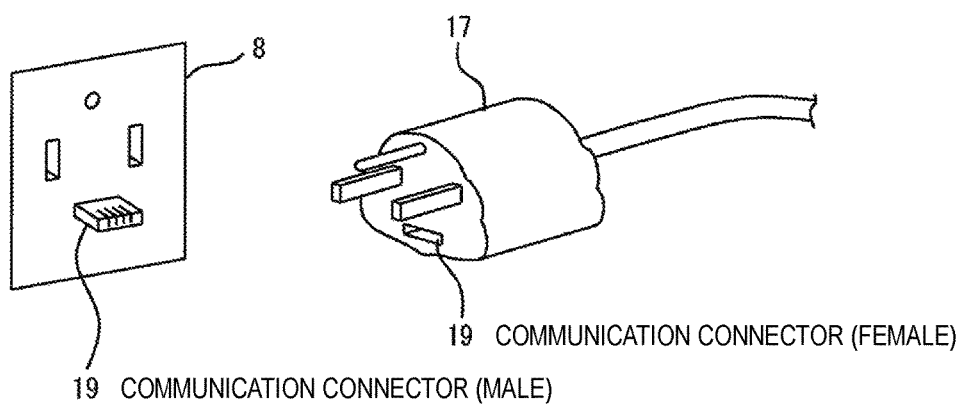
FIG. 18 is an exterior view of a communication connector 19.

Similar to the power supply device 200 (refer to the second embodiment and FIG. 11), the power supply device 300 includes the battery 12; the control unit 20; the current detector 26; and the power supply circuit 30. The power supply device 300 includes communication connectors 19 (refer to FIG. 18) having a communication function which are respectively provided in a plug 17 and the electrical outlet 8. The plug 17 and the electrical outlet 8 are connected to the communication unit 11.

In the embodiment, the control unit 20 includes the connection monitoring unit 21; the priority setting unit 22; the limit value acquisition unit 23; and the power limit signal unit 24.

(4.1.1 Connection Monitoring Unit 21)

The connection monitoring unit 21 detects connection between the mobile X-ray apparatus 1 and the wall electrical outlet 13 or other mobile X-ray apparatuses. If the connection is detected, the power supply device 300 communicates with power supply devices inside the other mobile X-ray apparatuses, and the power supply devices exchange information. In a case where the plug 17 is connected to a typical electrical outlet such as a wall electrical outlet not including a communication connector, the communication connector 19 is not activated.

(4.1.2 Priority Setting Unit 22)

The power supply device 300 includes the priority setting unit 22, which serves to set a charging priority, in the control unit 20. The priority setting unit 22 acquires priorities defined by a user via the input and output unit 9 and priorities defined by the other mobile X-ray apparatuses, and sets a charging priority.

(4.2 Flow of Process Performed by Control Unit 20)

Figure 19:
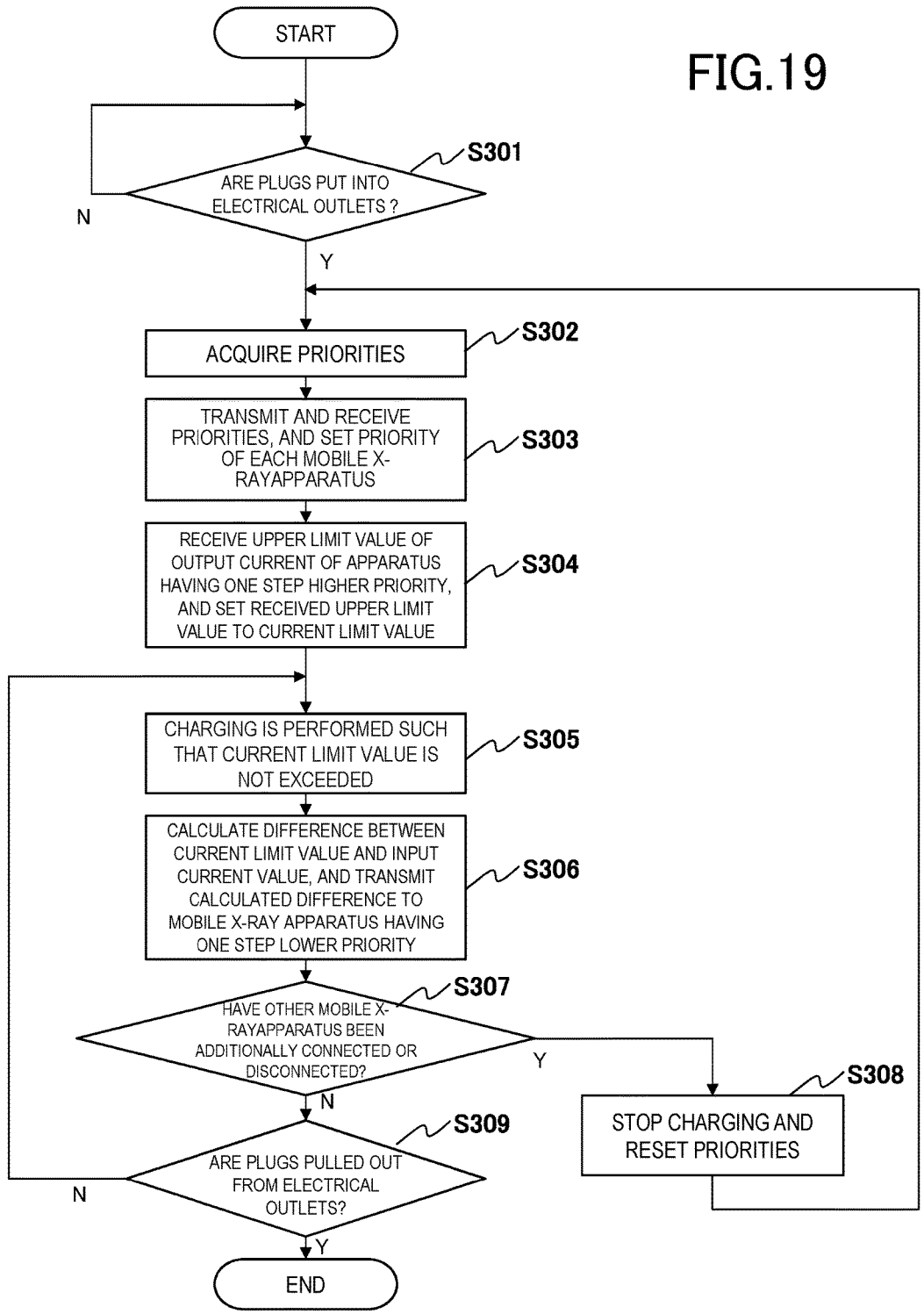
FIG. 19 is a flowchart illustrating a process performed by the control unit 20 of the third embodiment.

The flow of a process performed by the control unit 20 will be described with reference to a flowchart in FIG. 19.

For the preparation of charging, a user connects the plug 17 to the electrical outlet 8 or the wall electrical outlet 13 of a facility, and inputs a desired charging priority of each of the mobile X-ray apparatuses 1 via the input and output unit 9 (refer to FIG. 21(*d*)). Thereafter, the control unit 20 controls charging.

First, if the connection monitoring unit 21 of the control unit 20 detects that the plug 17 is connected to the electrical outlet 8 of another mobile X-ray apparatus or the wall electrical outlet 13 (Y in Step S301), the priority setting unit 22 of the control unit 20 acquires a charging priority, which is input by a user, from the input and output unit 9 (Step S302).

The priority is transmitted and received between other mobile X-ray apparatuses, and the priority setting unit 22 sets a priority of each mobile X-ray apparatus from the obtained priorities (Step S303). The priorities are determined in the ascending order of the numbers, and same numbers maybe omitted. In a case where the same number is input to multiple mobile X-ray apparatuses, a rule indicating that a mobile X-ray apparatus closer to a distal end of the connection has a higher priority is set in advance.

Subsequently, the limit value acquisition unit 23 of the control unit 20 receives a difference (upper limit value of an output current of a mobile X-ray apparatus having one step higher priority) between a current limit value and an input current value of the mobile X-ray apparatus having one step higher priority, and sets the upper limit value of the output current as a current limit value (Step S304). The power limit signal unit 24 of the control unit 20 charges the battery by generating the switch drive signal 25 and driving the semiconductor switch 32 in an on and off manner such that the current limit value is not exceeded (Step S305).

Subsequently, the control unit 20 calculates a difference (upper limit value of an output current of a host apparatus) between the current limit value and a current value of the input current, and transmits the difference to a mobile X-ray apparatus having one step lower priority (Step S306).

In a case where the number of connected mobile X-ray apparatuses is increased and decreased during charging, for example, a mobile X-ray apparatus is additionally connected or disconnected (Y in Step S307), the connection monitoring unit 21 of the control unit 20 detects this change, stops the charging, and resets the priorities (Step S308). Thereafter, the control unit 20 performs the process from Step S302 again.

(4.3 Current Limit Value in Case Where Three Apparatuses are Connected to Each Other)

Figure 20:
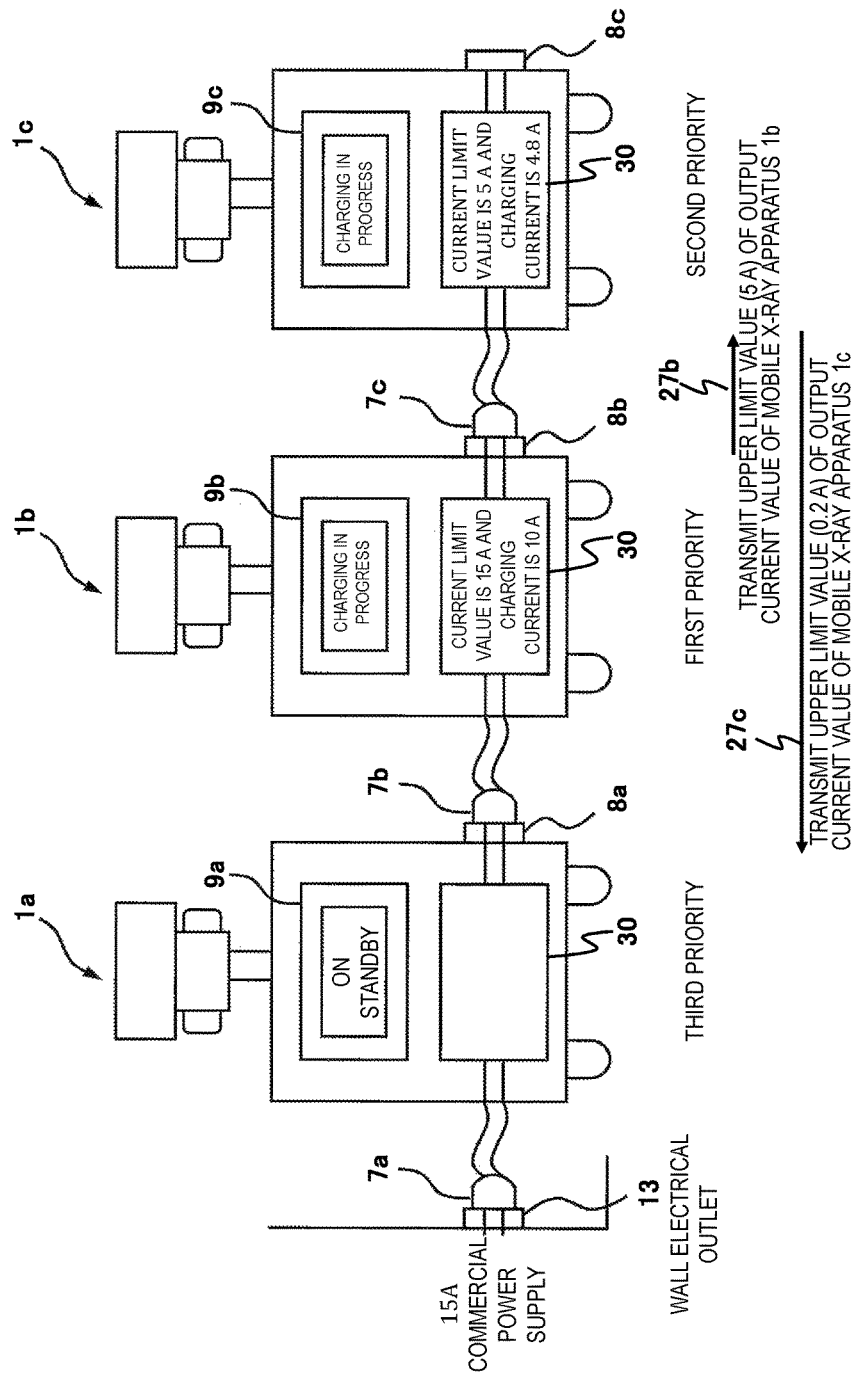
FIG. 20 is a schematic view illustrating the connected three mobile X-ray apparatuses 1 of the third embodiment.

As described above, the mobile X-ray apparatus 1 is charged. A case in which three mobile X-ray apparatuses 1 requiring charging are connected to each other will be specifically described with reference to FIG. 20. FIG. 20 schematically illustrates communication between apparatuses and current limit values and charging current values thereof in a case where the three mobile X-ray apparatuses 1*a*, 1*b*, and 1*c* are connected in series.

It is considered that the mobile X-ray apparatuses 1*a*, 1*b*, and 1*c* respectively have a third priority, a first priority, and a second priority (Step S303).

The mobile X-ray apparatus 1*b* having a first priority has a current limit value, for example, 15 [A] of a commercial power supply as a current limit value (Step S304).

The mobile X-ray apparatus 1*b* is charged such that the current limit value 15 [A] is not exceeded. If the charging current is set to 10 [A], the limitation of current is not required (Step S305).

The mobile X-ray apparatus 1*b* calculates a difference (upper limit value 27*b*, that is, 5 [A] of an output current value of the mobile X-ray apparatus 1*b*) between the current limit value 15 [A] and the charging current 10 [A], and transmits the difference to the mobile X-ray apparatus 1*c* (Step S306).

The mobile X-ray apparatus 1*c* having a second priority has the upper limit value 27*b* (5 [A]) of the output current value of the mobile X-ray apparatus 1*b* as a current limit value (Step S304). Since the current limit value of the mobile X-ray apparatus 1*c* is 5 [A], even if the mobile X-ray apparatus 1*c* originally requires the charging current 10 [A], an actual charging current is suppressed to 4.8 [A] due to the limitation of current (Step S305).

The mobile X-ray apparatus 1*b* calculates a difference (upper limit value 27*c*, that is, 0.2 [A] of an output current value of the mobile X-ray apparatus 1*c*) between the current limit value 5 [A] and the charging current 4.8 [A], and transmits the difference to the mobile X-ray apparatus 1a (Step S306).

Since the upper limit value 27c of the mobile X-ray apparatus 1a having a third priority is lower than the lower limit ($I_L$) of a current value for a charging operation, charging is not performed. As a result, a current 14.8 [A] (=10 [A]+4.8 [A]), which is the sum of the charging currents of the mobile X-ray apparatuses 1b and 1c, flows from the plug 17 of the mobile X-ray apparatus 1a to the electrical outlet 8a. Accordingly, an output current from the wall electrical outlet 13 is suppressed to 15 [A] or less, and charging is safely performed according to the priority order of the mobile X-ray apparatuses 1b, 1c, and 1a.

The upper limit values of the charging current values may be set in advance according to the priorities, for example, the upper limit values may be respectively set to 12 [A], 3 [A], and 0 [A] for a first priority, a second priority, and third and subsequent priorities, or only a mobile X-ray apparatus having a first priority may be set to be charged with the current limit value of the commercial power supply.

(4.4 Effects of Connection Charging)

As described above, in a case where the multiple mobile X-ray apparatuses 1a, 1b, and 1c are connected to each other via the power supply devices 300, it is possible to safely proceed with charging according to priorities of the mobile X-ray apparatuses defined by a user while making the most of current up to the current capacity of the one wall electrical outlet 13. For example, if a user selects a mobile X-ray apparatus having a high usage frequency to have the "highest" charging priority via the input and output unit 9 (refer to FIG. 21(d)), the user can preferentially charge the mobile X-ray apparatus without paying attention to the order of connecting plugs, and it is possible to use the mobile X-ray apparatuses methodically.

If a mobile X-ray apparatus having a low battery capacity is selected to have a high priority, the length of time to the completion of charging is short, and thus, it is possible to prepare a mobile X-ray apparatus soon, the charging of which is complete, and to increase the operation rate of the mobile X-ray apparatus.

In a case where the number of connected mobile X-ray apparatuses is increased or decreased, the priorities are reset, and then charging is started. At this time, it is not necessary for a user to manage charging, and the use of the mobile X-ray apparatus of the embodiment is very convenient.

Accordingly, in the embodiment, even if a user connects together multiple mobile X-ray apparatuses without paying attention to a charging priority, it is possible to perform charging according to a desired priority, and convenience is improved.

(4.5 Application Examples)

Figure 22:
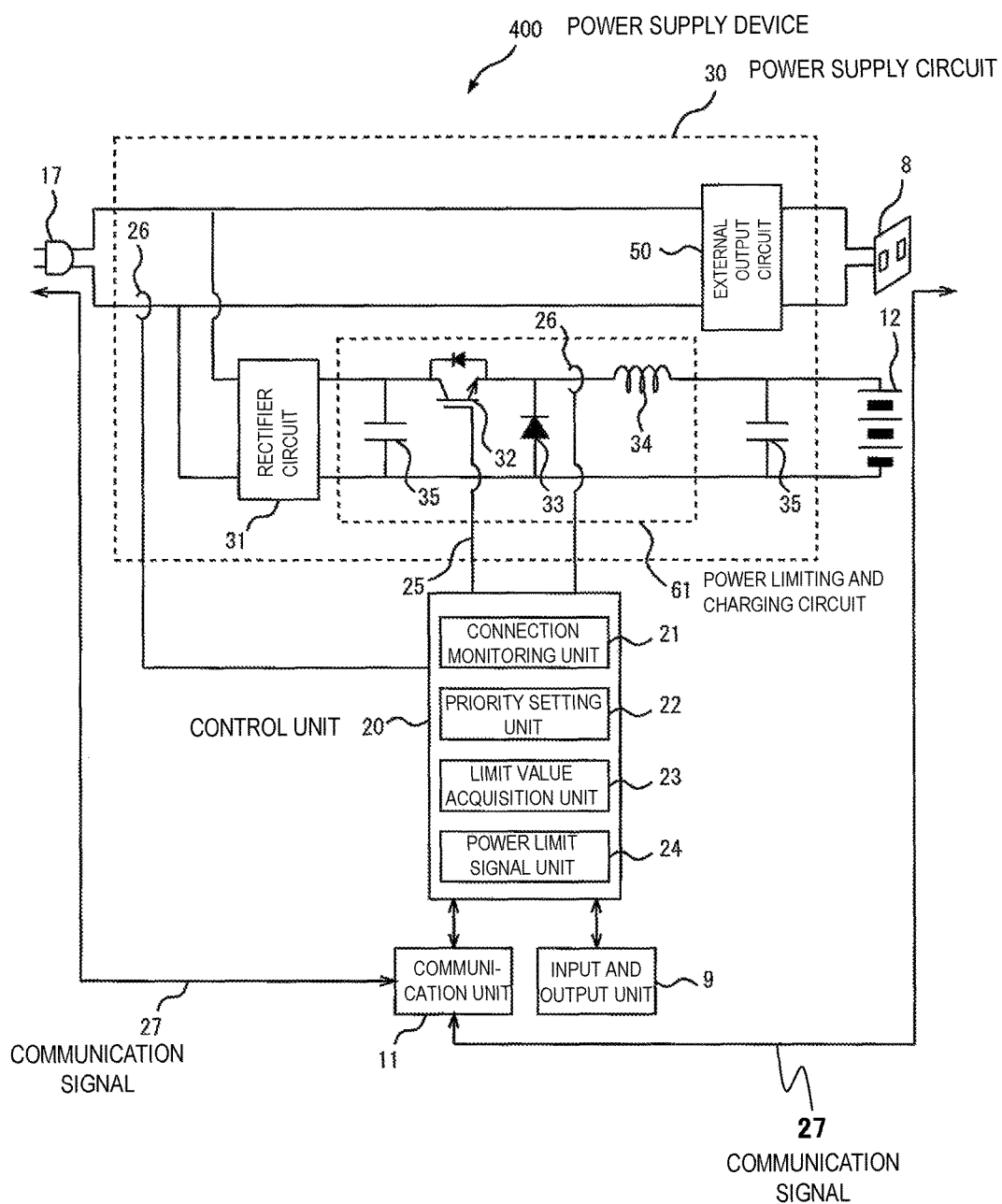
FIG. 22 is a diagram illustrating the function and circuit configuration of a power supply device 400 using the power limiting and charging circuit 61.

Similar to the power supply circuit 30 illustrated in FIG. 22, the power limiting and charging circuit 61 which serves as both a power limiting circuit and a charging circuit may be used. As a result, it is possible to decrease the size and power loss of the power supply circuit.

In the embodiment, the communication connectors 19 are respectively built into the plug 17 and the electrical outlet 8, and the detection of connection and communication are performed via cables. Alternatively, the detection of connection may be performed by detecting the potential of the plug or by a sensor, and communication may be performed wirelessly.

(4.6 Mobile X-ray Apparatus, Method for Charging Mobile X-ray Apparatus, and Power Supply Device of Embodiment)

The mobile X-ray apparatus, the method for charging a mobile X-ray apparatus, and the power supply device of the embodiment provide the same effects as those in the second embodiment.

The control unit 20 of the embodiment desirably includes the connection monitoring unit 21 that detects connection between a host mobile X-ray apparatus and other mobile X-ray apparatuses when charging is performed; the priority setting unit 22 that sets a priority of charging performed by each of the connected power supply devices 300 in a case where the connection monitoring unit 21 detects the connection; and the limit value acquisition unit 23 that receives an upper limit value of an output current output from the mobile X-ray apparatus 1 having one step higher priority, and sets the received upper limit value as a current limit value. Desirably, the control unit 20 calculates the upper limit value of the output current which is a difference between the current limit value and the current value of the input current, and transmits the calculated upper limit value to the mobile X-ray apparatus 1 having one step lower priority.

Accordingly, it is possible to proceed with charging according to charging priorities defined by a user. In a case where the number of connected mobile X-ray apparatuses is increased or decreased, the priorities are reset, and then charging is started. At this time, it is not necessary for a user to manage charging, and the use of the mobile X-ray apparatus of the embodiment is very convenient.

In the embodiment, there is provided the method for charging the mobile X-ray apparatus 1, desirably, the method further including: a connection detection step (S301) of detecting connection between a host mobile X-ray apparatus and other mobile X-ray apparatuses; a priority setting step (S303) of setting a priority of charging performed by each of the connected power supply devices 300 in a case where the connection is detected; a limit value acquisition step (S304) of receiving an upper limit value of an output current output from the mobile X-ray apparatus 1 having one step higher priority, and setting the received upper limit value as a current limit value; and a step (S306) of calculating the upper limit value of the output current which is a difference between the current limit value and a current value of an input current, and transmitting the calculated upper limit value to the mobile X-ray apparatus 1 having one step lower priority.

(5 Fourth Embodiment)

A fourth embodiment of the mobile X-ray apparatus of the invention will be described. In the embodiment, suitably, multiple mobile X-ray apparatuses 1 are connected to each other, priorities are automatically determined in accordance with apparatus information regarding each mobile X-ray apparatus, for example, a operation schedule such as an order number which is the number of captured images or battery capacity performance, and charging is performed.

The mobile X-ray apparatus of the embodiment is capable of using the power supply device 300 (refer to FIG. 17) described in the third embodiment. The priority setting unit 22 of the control unit 20 has the function of acquiring apparatus information regarding each mobile X-ray apparatus, and setting a charging priority.

(5.1 Flow of Process Performed by Control Unit 20)

Figure 23:
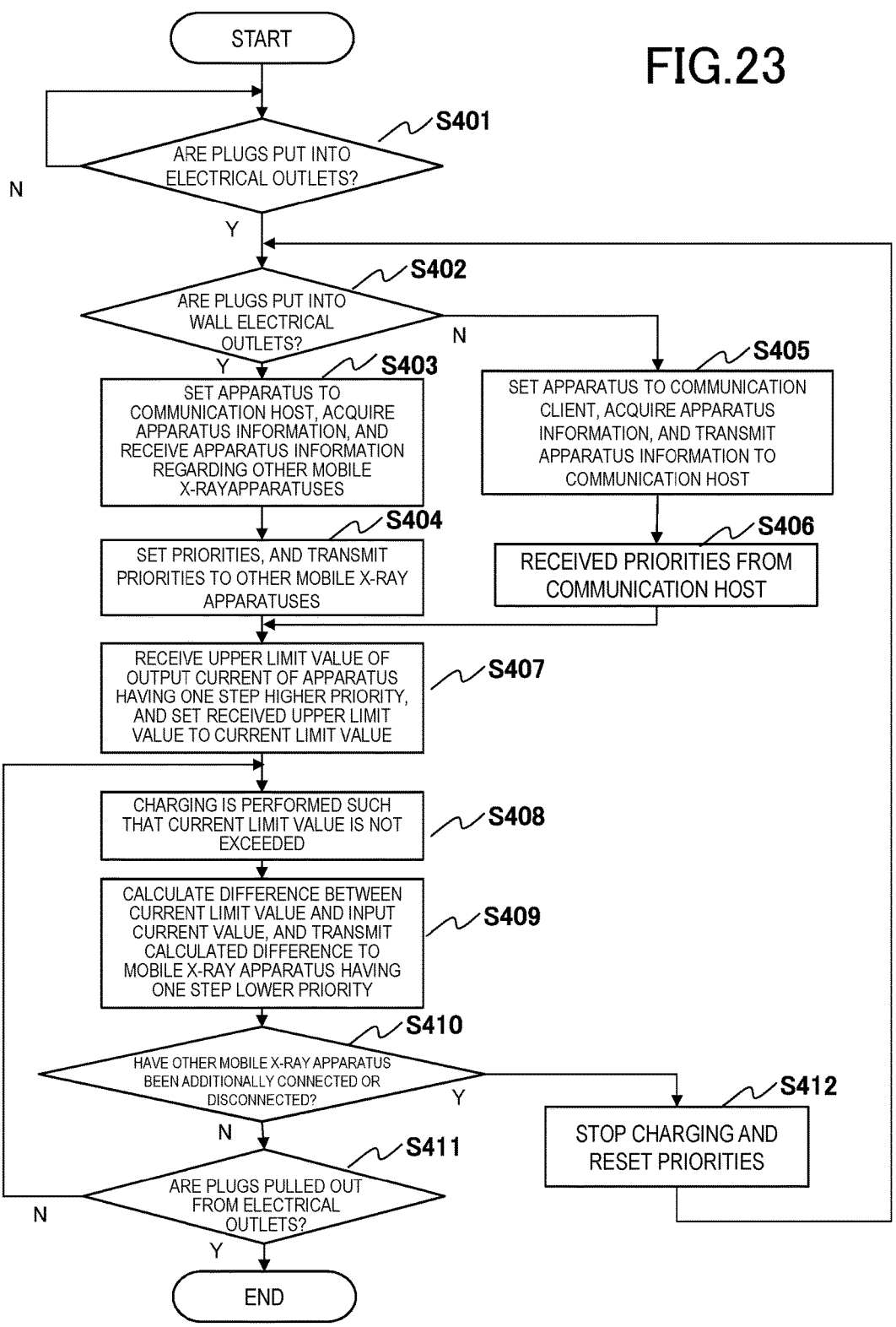
FIG. 23 is a flowchart illustrating a process performed by the control unit 20 of the fourth embodiment.

The flow of a process performed by the control unit 20 will be described with reference to a flowchart in FIG. 23.

For the preparation of charging, a user connects together the mobile X-ray apparatuses similar to that in the third embodiment. Each mobile X-ray apparatus registers the predetermined number of images (hereinafter, referred to as an order number) captured after the completion of charging, which is apparatus information, in a storage unit (not illustrated) in advance. Thereafter, the control unit 20 controls charging according to an order number for each mobile X-ray apparatus. The larger order number a mobile X-ray apparatus has, the sooner the charging of the mobile X-ray apparatus is required to be complete, and thus, a high charging priority is assigned thereto.

First, the connection monitoring unit 21 of the control unit 20 detects that the plug 17 is connected to the electrical outlet 8 of another mobile X-ray apparatus or the wall electrical outlet 13 (Y in Step S401). If it is detected that the plug 17 is connected to the wall electrical outlet 13 of a facility (Y in Step S402), the mobile X-ray apparatus becomes a communication host, and the control unit 20 acquires an order number, which is apparatus information, from the storage unit (not illustrated) and receives order numbers for other mobile X-ray apparatuses (Step S403).

The priority setting unit 22 of the control unit 20 preferentially sets a priority of a mobile X-ray apparatus having a large order number, and transmits the priority to other mobile X-ray apparatuses (Step S404). In a case where the same number of orders is registered for multiple mobile X-ray apparatuses, a rule indicating that a mobile X-ray apparatus closer to a distal end of the connection has a higher priority is set in advance.

In contrast, in a case where the plug 17 is connected to the electrical outlet 8 of another mobile X-ray apparatus in Step S402 (N in Step S402), the control unit 20 becomes a communication client, acquires an order number, which is apparatus information, from the storage unit (not illustrated), and transmits the order number to a mobile X-ray apparatus which is a communication host (Step S405). Thereafter, the control unit 20 receives the priority from the mobile X-ray apparatus which is a communication host (Step S406).

The following Steps S407 to S412 are performed similar to Steps S305 to S309 (refer to FIG. 19) in the third embodiment. After, in Step S412, the charging stops, and the priorities are reset, the control unit 20 performs the process from Step S402 again.

(5.2 Effects of Connection Charging)

As described above, it is possible to proceed with the charging of the mobile X-ray apparatuses of the embodiment according to charging priorities set based on apparatus information. If a user selects a mode ("auto" which is an example of display illustrated in FIG. 21(*d*)), in which mobile X-ray apparatuses automatically set priorities, via the input and output unit 9, it is possible to charge the mobile X-ray apparatuses in an order optimized for operation schedules.

If a mobile X-ray apparatus having a large order number is set to be preferentially charged, it is possible to complete the charging of the apparatus having a larger order number sooner than other apparatuses, and it is possible to use the apparatus soon. As a result, it is possible to decrease the number of user's operation sequences such as taking priorities into consideration, and to improve the operation rates of the mobile X-ray apparatuses. In addition, apparatus information used to determine a charging priority includes a battery residual capacity, the number of times of use of an apparatus, a reserved order status, a distance to a service place (a patient room, a treatment room, or the like), a go-round start time, and the like.

It is possible to preferentially charge a mobile X-ray apparatus unusable due to a low battery by assigning a high priority to an apparatus having a low battery residual capacity.

It is possible to minimize a difference in the number of times of use between multiple mobile X-ray apparatuses by assigning a higher priority to a mobile X-ray apparatus of which the number of time of use is smaller than other mobile X-ray apparatuses. Accordingly, it is possible to prevent the progress of consumption of consumables, for example, an X-ray tube and a battery of only a specific mobile X-ray apparatus, and it is possible to extend the life span of the mobile X-ray apparatus.

The mobile X-ray apparatus of the embodiment may use a power supply device 400 (refer to FIG. 22) rather than the power supply device 300.

(5.3 Mobile X-ray Apparatus, Method for Charging Mobile X-ray Apparatus, and Power Supply Device of Embodiment)

The mobile X-ray apparatus, the method for charging a mobile X-ray apparatus, and the power supply device of the embodiment provide the same effects as those in the third embodiment.

In the embodiment, there is provided the method for charging the mobile X-ray apparatus 1, desirably, the method further including: a connection detection step (S401) of detecting connection between a host mobile X-ray apparatus and other mobile X-ray apparatuses; a priority setting step (S404) of setting a priority of charging performed by each of the connected power supply devices 300 in a case where the connection is detected; a limit value acquisition step (S407) of receiving an upper limit value of an output current output from the mobile X-ray apparatus 1 having one step higher priority, and setting the received upper limit value as a current limit value; and a step (S409) of calculating the upper limit value of the output current which is a difference between the current limit value and a current value of an input current, and transmitting the calculated upper limit value to the mobile X-ray apparatus 1 having one step lower priority.

(6 Fifth Embodiment)

A fifth embodiment of the mobile X-ray apparatus of the invention will be described. In the embodiment, multiple mobile X-ray apparatuses 1 are capable of suitably supplying and receiving power therebetween.

(6.1 Power Supply Device 500)

Figure 24:
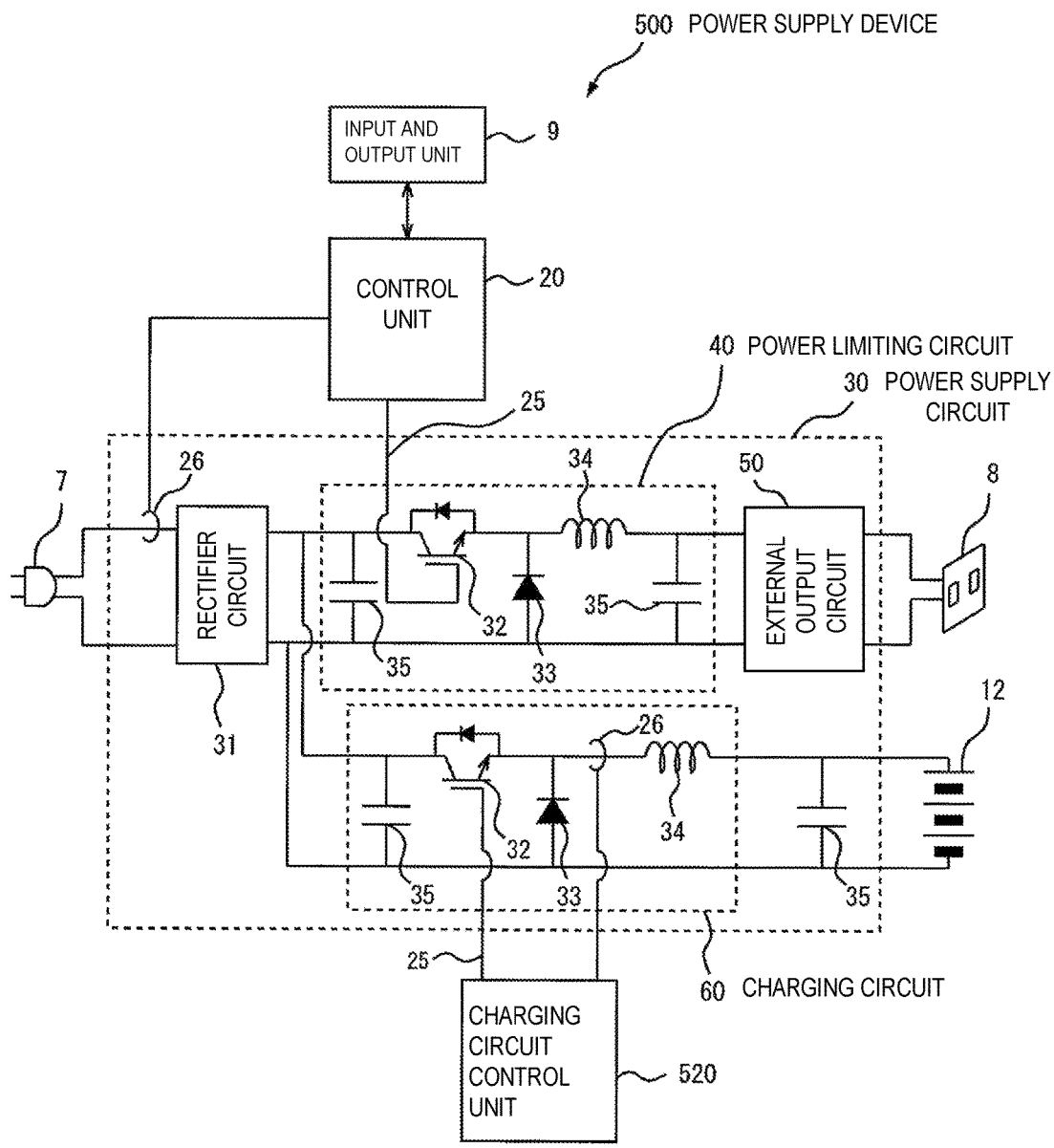
FIG. 24 is a diagram illustrating the function and circuit configuration of a power supply device 500 of a fifth embodiment.

FIG. 24 illustrates a power supply device 500.

Similar to the power supply device 10 (refer to the first embodiment and FIG. 4), the power supply device 500 includes the power limiting circuit 40; a charging circuit control unit 520; and the charging circuit 60. The charging circuit 60 is formed of a stepdown chopper circuit.

(6.2 Operation of Power Supply Circuit 30 in Case Where Two Apparatuses are Connected to Each Other)

Figure 25:
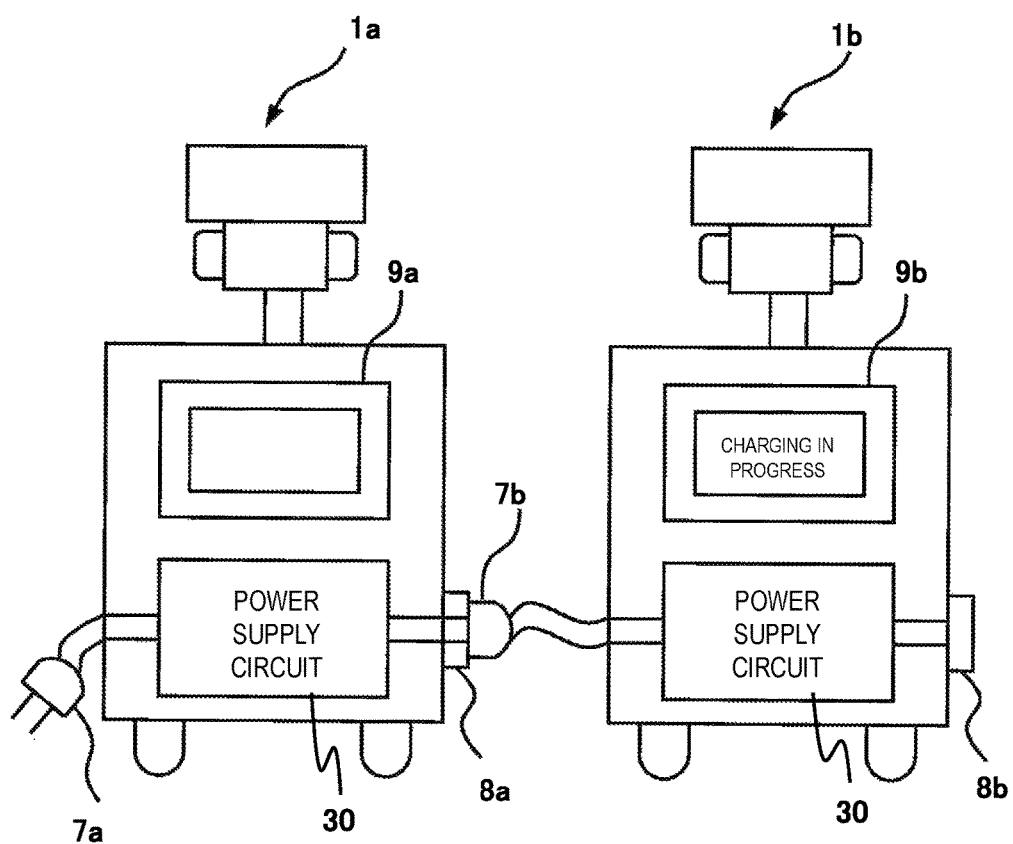
FIG. 25 is a schematic view illustrating the connected two mobile X-ray apparatuses 1 of the fifth embodiment.

In a case where the plug 7*a* of the mobile X-ray apparatus 1*a* is not connected to an electrical outlet, and the plug 7*b* of the mobile X-ray apparatus 1*b* is connected to the electrical outlet 8*a*, power is supplied from the mobile X-ray apparatus 1*a* to the mobile X-ray apparatus 1*b* (refer to FIG. 25).

Specifically, the power of the battery 12 of the mobile X-ray apparatus 1*a* is supplied to the power limiting circuit 40 via the inductor 34 and the semiconductor switch 32.

If power is supplied to the mobile X-ray apparatus 1*b* via the electrical outlet 8*a* and the plug 7*b*, the power is input to the charging circuit 60. The charging circuit 60 supplies voltage current, which is suitable for charging, to the battery. Accordingly, it is possible to charge the battery 12 of the mobile X-ray apparatus 1*b* with the power supplied to the charging circuit 60 of the mobile X-ray apparatus 1*b*.

(6.3 Effects of Connection Charging)

As described above, the connected mobile X-ray apparatuses of the embodiment are capable of supplying and receiving power therebetween. Such a charging function is greatly useful particularly in the following cases.

In a case where, while a user goes the rounds using two mobile X-ray apparatuses, the battery residual capacity of one mobile X-ray apparatus becomes low, and the one mobile X-ray apparatus is not capable of taking an X-ray, if the other mobile X-ray apparatus has a sufficient battery residual capacity, it is possible to replenish a power shortage via the aforementioned method, and to use both the mobile X-ray apparatuses.

The use of the one mobile X-ray apparatus has to be stopped thus far. In contrast, if the mobile X-ray apparatuses of the embodiment are used, the user can continuously go the rounds using the two apparatuses, and thus, it is possible to reduce the length of time required to go the rounds by half. This function is very useful in a disaster area or the like in which charging infrastructures are insufficient.

In a case where a mobile X-ray apparatus is not capable of travelling using electricity due to a dead battery, it is possible to charge the dead battery, and to allow the mobile X-ray apparatus to travel with electricity by preparing a mobile X-ray apparatus having a sufficient battery residual capacity, and supplying power from this mobile X-ray apparatus.

Since a lot of and very heavy components such as an X-ray tube and a battery are mounted in a mobile X-ray apparatus, it is difficult to move a mobile X-ray apparatus which is in a state of being unable to travel without electricity. In a case where there is no electrical outlet in the reach of a charging cable, multiple persons are required to push and move the apparatus. In contrast, in a case where the mobile X-ray apparatuses of the embodiment are used, even if a battery is dead, one user can cope with the situation, and it is possible to decrease an impact on clinical services.

In the embodiment, multiple electrical outlets 8 may be adopted, and multiple mobile X-ray apparatuses maybe connected thereto.

The power supply devices 10, 200, 300, 400, and 500 described in the first to fifth embodiments may be used in X-ray apparatuses other than a mobile X-ray apparatus. The power supply devices 10, 200, 300, 400, and 500 maybe used as a power supply device for an X-ray apparatus mounted on a vehicle for going the rounds or for a physical examination. In this case, it is possible to obtain power from an electrical outlet of a facility close to an imaging place, and thus, there is no need to mount an engine generator, that is a power supply, in the vehicle. As a result, preparation made by a user becomes simple, and convenience is improved.

In the specific description given in the embodiments, three mobile X-ray apparatuses are connected to each other and are charged; however, in the invention, the number of connected mobile X-ray apparatuses is not limited to a specific number. Even if two apparatuses are connected to each other, it is possible to obtain the effects of the invention. Even if the power supply devices 10, 200, 300, 400, and 500 are removed from X-ray apparatuses, and multiple supply devices are connected to each other and are charged, it is possible to obtain the same effects of the invention.

In the third embodiment, the communication connectors 19 are respectively built into the plug 17 and the electrical outlet 8, and the detection of connection and communication are performed via cables. In the application example thereof, the detection of connection is performed by detecting the potential of the plug or by a sensor, and communication is performed wirelessly. There may be provided a mobile X-ray apparatus that takes an X-ray using power charged therein, and includes a power supply device that divides a power, which is input from external equipment, into at least two powers, distributes one power of the divided powers to an external output circuit, outputs the power to external equipment, distributes the other power to a charging circuit, and charges the apparatus with the power. The power supply device may include a current detector that detects a current value of the input power; a power limiting circuit that limits at least one of the power distributed to the external output circuit and the power distributed to the charging circuit; and a control unit that controls current flowing in the power limiting circuit based on the current value detected by the current detector. The control unit may include a connection monitoring unit that detects connection between a host mobile X-ray apparatus and other mobile X-ray apparatuses when charging is performed; a priority setting unit that sets a priority of charging performed by each of the connected power supply devices in a case where the connection monitoring unit detects the connection; and a limit value acquisition unit that, in a case where the limit value acquisition unit acquires a current limit value from a storage unit which is the maximum value of current that can be input from external equipment, or receives a current limit value from another mobile X-ray apparatus, acquires a smaller current limit value of the current limit values as a current limit value. The control unit may calculate a current limit value which is a difference between the current limit value and the current value detected by the current detector and is the maximum value of current that can be input from external equipment to a mobile X-ray apparatus having one step lower priority, and transmit the calculated current limit value to a mobile X-ray apparatus having one step lower priority.

As such, an individual mobile X-ray apparatus is capable of acquiring a current limit value which is the maximum value of current that can be input from external equipment, and the individual mobile X-ray apparatus can be charged with power from the external equipment such that the current limit value is not exceeded. As a result, multiple mobile X-ray apparatuses are respectively connected to multiple wall electrical outlets 13, charging priorities are set, and the mobile X-ray apparatuses can be charged while the sum of current supplied from the multiple wall electrical outlets 13 is confirmed such that the current capacities of power supply source are not exceeded.

The preferred embodiments of the invention have been described with the accompanying drawings; however, the invention is not limited to the embodiments. It is apparent to persons skilled in art that various changes or modifications can be made within the technical concept disclosed in this specification. Naturally, it is ascertained that the various changes or modifications are also included in the technical scope of the invention.

INDUSTRIAL APPLICABILITY

The invention is useful as a method for charging a mobile X-ray apparatus, and provides a mobile X-ray apparatus that is capable of safely charging multiple mobile X-ray apparatuses.

REFERENCE SIGNS LIST

1, 1*a*, 1*b*, 1*c*: mobile X-ray apparatus
2: main body
3: trolley 4: support column
5: arm
6: X-ray unit
7, 7a, 7b, 7c: plug
8, 8a, 8b, 8c: electrical outlet
9, 9a, 9b, 9c: input and output unit
10: power supply device
11: communication unit
12: battery
13: wall electrical outlet
17: plug
19: communication connector
20: control unit
21: connection monitoring unit
22: priority setting unit
23: limit value acquisition unit
24: power limit signal unit
25: switch drive signal
26: current detector
30: power supply circuit
31: rectifier circuit
32: semiconductor switch
33: diode
34: inductor
35: capacitor
36: semiconductor switch
40, 41: power limiting circuit
50, 51: external output circuit
60: charging circuit
61: power limiting and charging circuit
200, 300, 400, 500: power supply device
520: charging circuit control unit

The invention claimed is:

1. A mobile X-ray apparatus that takes an X-ray using power charged therein, the apparatus comprising:
a power supply device that divides an input power which is input from first external equipment, into at least two powers as divided powers, connects one power of the divided powers to an external output circuit to output the power to second external equipment, and connects the other power to a charging circuit to charge the apparatus with the power,
wherein the power supply device includes:
a current detector that detects a current value of the input power;
a power limiting circuit that limits at least one of the one power output to the external output circuit and the other power output to the charging circuit; and
a control unit that controls current flowing in the power limiting circuit based on the current value detected by the current detector;
wherein the power supply device distributes an input current which is input from the first external equipment, to at least two current paths as distributed current paths,
wherein a first current path of the at least the two current paths is connected to the second external output circuit, and allows an external output current to flow therein,
wherein a second current path of the at least the two current paths is connected to the charging circuit, and allows a charging current to flow therein,
wherein the power limiting circuit limits at least one of the external output current and the charging current,
wherein the current detector detects a current value of the input current, and
wherein the control unit controls at least one of the external output current flowing in the power limiting circuit and the charging current such that the current value of the input current detected by the current detector becomes equal to or less than a current limit value that is a maximum value of current which can be input from the first external equipment,
wherein the control unit includes:
a connection monitoring unit that detects connection between the apparatus as a host mobile X-ray apparatus and other mobile X-ray apparatuses, when charging is performed;
a priority setting unit that sets a priority of charging performed by each of connected power supply devices of the apparatus and the other mobile X-ray apparatuses in a case where the connection monitoring unit detects the connection; and
a limit value acquisition unit that receives an upper limit value of an external output current output from a mobile X-ray apparatus having one step higher priority, and sets the received upper limit value as a current limit value, and
wherein the control unit calculates the upper limit value of the external output current which is a difference between the current limit value and the current value of the input current, and transmits the calculated upper limit value to a mobile X-ray apparatus having one step lower priority.

2. The mobile X-ray apparatus according to claim 1, wherein the power limiting circuit is provided in a front stage of the external output circuit, and limits current flowing in the external output circuit.

3. The mobile X-ray apparatus according to claim 1, wherein the power limiting circuit is provided in a front stage of the charging circuit, and limits current flowing in the charging circuit.

4. The mobile X-ray apparatus according to claim 1, wherein the power limiting circuit includes a semiconductor switch which settably increases and decreases the amount of current flowing in the power limiting circuit via opening and closing, and
wherein the control unit controls the opening and closing of the semiconductor switch.

5. The mobile X-ray apparatus according to claim 1, wherein the power limiting circuit limits current flowing in the external output circuit, and
wherein the charging circuit limits current flowing in the charging circuit, and charges a battery of the mobile X-ray apparatus.

6. A method for charging plural X-ray apparatus that each include a power supply device which divides an input power which is input from input external equipment into at least two powers as divided powers, connects one power of the divided powers to an external output circuit to output the one power to output external equipment, connects the other power to a charging circuit to charge the mobile X-ray apparatus with the other power, and that takes an X-ray using power charged therein, the method comprising:
a current detection step of detecting a current value of the input power;
a power limitation step of limiting at least one of the one power output to the external output circuit and the other power output to the charging circuit, based on the current value detected in the current detection step;
a connection detection step of detecting connection of plural mobile X-ray apparatuses as connected mobile X-ray apparatuses;

a priority setting step of setting a priority of charging performed by each of connected power supply devices of the connected mobile X-ray apparatuses in a case where the connection is detected;

and for a connected mobile X-ray apparatus of the connected X-ray apparatuses, performing:

a limit value acquisition step of receiving an upper limit value of an external output current output from a higher-priority connected mobile X-ray apparatus having one step higher priority, and setting the received upper limit value as a current limit value for the connected mobile X-ray apparatus; and a step of calculating the upper limit value of an external output current outputted from the connected mobile X-ray apparatus, which is a difference between the current limit value and the current value detected in the current detection step, and transmitting the calculated upper limit value to a lower-priority connected mobile X-ray apparatus having one step lower priority.

7. The method for charging a mobile X-ray apparatus according to claim 6,
wherein in the power limitation step, at least one of current flowing in the external output circuit and current flowing in the charging circuit is limited such that the current value detected in the current detection step becomes equal to or less than a current limit value that is the maximum value of current which can be input from the external equipment.

8. A mobile X-ray apparatus that takes an X-ray using power charged therein, the apparatus comprising:
a power supply device that divides a power, which is input from external equipment, into at least two powers, connects one power of the divided powers to an external output circuit, outputs the power to external equipment, connects the other power to a charging circuit, and charges the apparatus with the power, wherein the power supply device includes
a current detector that detects a current value of the input power;
a power limiting circuit that limits at least one of the power output to the external output circuit and the power output to the charging circuit; and
a control unit that controls current flowing in the power limiting circuit based on the current value detected by the current detector, wherein the control unit includes
a connection monitoring unit that detects connection between a host mobile X-ray apparatus and other mobile X-ray apparatuses when charging is performed;
a priority setting unit that sets a priority of charging performed by each of the connected power supply devices of a mobile X-ray apparatus in a case where the connection monitoring unit detects the connection; and
a limit value acquisition unit that, in a case where the limit value acquisition unit acquires a current limit value from a storage unit which is the maximum value of current that can be input from external equipment, or receives a current limit value from another mobile X-ray apparatus, acquires a smaller current limit value of the current limit values as a current limit value, wherein the control unit calculates a current limit value which is a difference between the current limit value and the current value detected by the current detector and is the maximum value of current that can be input from external equipment to a mobile X-ray apparatus having one step lower priority, and transmits the calculated current limit value to a mobile X-ray apparatus having one step lower priority.

* * * * *